US008680065B2

(12) United States Patent
Xu et al.

(10) Patent No.: US 8,680,065 B2
(45) Date of Patent: Mar. 25, 2014

(54) OLIGONUCLEOTIDES OF HUMAN ENDOGENOUS RETROVIRUS 9 (ERV-9) LONG TERMINAL REPEAT (LTR) AND METHODS OF USE

(75) Inventors: Lai Xu, North Potomac, MD (US); Amy S. Rosenberg, Kensington, MD (US); Abdel Elkahloun, Bethesda, MD (US); Fabio Candotti, Brookville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/062,858

(22) PCT Filed: Sep. 11, 2009

(86) PCT No.: PCT/US2009/056722
§ 371 (c)(1),
(2), (4) Date: Mar. 8, 2011

(87) PCT Pub. No.: WO2010/030931
PCT Pub. Date: Mar. 18, 2010

(65) Prior Publication Data
US 2011/0166204 A1  Jul. 7, 2011

Related U.S. Application Data

(60) Provisional application No. 61/191,911, filed on Sep. 11, 2008.

(51) Int. Cl.
*C12N 15/11* (2006.01)
*C07H 21/04* (2006.01)
*C12Q 1/68* (2006.01)

(52) U.S. Cl.
USPC ............... 514/44 A; 536/24.5; 435/6.11

(58) Field of Classification Search
USPC ............... 514/44 A; 536/24.5; 435/6.11
See application file for complete search history.

(56) References Cited

U.S. PATENT DOCUMENTS

| 6,001,987 | A | 12/1999 | Perron et al. |
| 6,184,025 | B1 | 2/2001 | Perron et al. |
| 6,365,727 | B1 | 4/2002 | Yoon et al. |
| 6,395,549 | B1 | 5/2002 | Tuan et al. |
| 6,582,703 | B2 | 6/2003 | Perron et al. |
| 6,582,908 | B2 * | 6/2003 | Fodor et al. .......... 506/9 |
| 6,919,438 | B1 | 7/2005 | Alliel et al. |
| 7,163,927 | B2 | 1/2007 | Dobie et al. |
| 7,381,817 | B2 | 6/2008 | Paranhos-Baccala et al. |

FOREIGN PATENT DOCUMENTS

| EP | 1847620 | 10/2007 |
| WO | WO 03/050258 | 6/2003 |
| WO | WO 03/070757 | 8/2003 |
| WO | WO 2004/037972 | 5/2004 |
| WO | WO 2004/096021 | 11/2004 |
| WO | WO 2006/103562 | 10/2006 |

OTHER PUBLICATIONS

Genebank Accession No. DQ583023 (submitted 2006).*
Girard et al. (Nature (2006) 442:199-202).*
Clausen, "Endogenous retroviruses and MS: Using ERVs as disease markers," *The International MS Journal*, vol. 10:22-28, 2003.
Costas & Naveira, "Evolutionary History of the Human Endogenous Retrovirus Family ERV9," *Mol. Biol. Evol.*, vol. 17(2):320-330, 2000.
Dean & Bennett, "Antisense oligonucleotide-based therapeutics for cancer," *Oncogene*, vol. 22:9087-9096, 2003.
Di Cristofano et al., "Characterization and genomic mapping of the ZNF80 locus: expression of this zinc-finger gene is driven by a solitary LTR of ERV9 endogenous retroviral family," *Nucleic Acids Research*, vol. 23(15):2823-2830, 1995.
Frank et al., "Human endogenous retrovirus expression profiles in samples from brains of patients with schizophrenia and bipolar disorders," *J. Virol.*, vol. 79(17):10890-10901, 2005.
Karlsson et al., "Retroviral RNA identified in the cerebrospinal fluids and brains of individuals with schizophrenia," *Proc. Natl. Acad. Sci. USA*, vol. 98(8):4634-4639, Apr. 10, 2001.
La Mantia et al., "Identification and characterization of novel human endogenous retroviral sequences preferentially expressed in undifferentiated embryonal carcinoma cells," *Nucleic Acids Research*, vol. 19(7):1513-1520, 1991.
La Mantia et al., "Identification of regulatory elements within the minimal promoter region of the human endogenous ERV9 proviruses: accurate transcription initiation is controlled by an Inr-like element," *Nucleic Acids Res.*, vol. 20(16):4129-4136, 1992.
Lania et al., "Structural and Functional Organization of the Human Endogenous Retroviral ERV9 Sequences," *Virol.*, vol. 191:464-468, 1992.
Lindeskog et al., "Sequence variation of human endogenous retrovirus ERV9-related elements in an *env* region corresponding to an immunosuppressive peptide: transcription in normal and neoplastic cells," *J. of Virol.*, vol. 67(2):1122-1126, 1993.

(Continued)

*Primary Examiner* — Jon E Angell
(74) *Attorney, Agent, or Firm* — Klarquist Sparkman, LLP

(57) ABSTRACT

Described herein are oligonucleotides that target the human endogenous retrovirus-9 (ERV-9) long terminal repeat (LTR). The ERV-9 LTR oligonucleotides specifically hybridize with either the coding strand or non-coding strand of ERV-9 LTR. It is disclosed herein that ERV-9 LTR oligonucleotides inhibit the proliferation of cancer cells, including breast cancer, liver cancer, prostate cancer, fibrosarcoma and myeloid cancer cells. Also described herein are methods of treating a subject diagnosed with cancer comprising administering to the subject an ERV-9 LTR oligonucleotide. In some examples, the methods further comprise administering a second therapeutic agent, such as an antisense compound or a chemotherapeutic agent.

23 Claims, 13 Drawing Sheets

(56) References Cited

OTHER PUBLICATIONS

Ling et al., "The ERV-9 LTR enhancer is not blocked by the HS5 insulator and synthesizes through the HS5 site non-coding, long RNAs that regulate LTR enhancer function," *Nucleic Acids Research*, vol. 31(15):4582-4596, 2003.

Ling et al., "The solitary long terminal repeats of ERV-9 endogenous retrovirus are conserved during primate evolution and possess enhancer activities in embryonic and hematopoietic cells," *J. Virol.*, vol. 76(5):2410-2423, 2002.

Molés et al., "A new endogenous retroviral sequence is expressed in skin of patients with psoriasis," *British J. Derm.*, vol. 153:83-89, 2005.

Perron et al., "Molecular identification of a novel retrovirus repeatedly isolated from patients with multiple sclerosis," *Proc. Natl. Acad. Sci. USA*, vol. 94:7583-7588, 1997.

Pi et al., "The LTR enhancer of ERV-9 human endogenous retrovirus is active in oocytes and progenitor cells in transgenic zebrafish and humans," *Proc. Natl. Acad. Sci. USA*, vol. 101(3):805-810, 2004.

Schott et al., "Efficient recovery and regeneration of integrated retroviruses," *Nucleic Acids Research*, vol. 25(14):2940-2942, 1997.

Strazzullo et al., "Characterization and Genomic Mapping of Chimeric ERV9 Endogenous Retroviruses-Host Gene Transcripts," *Gene*, vol. 206:77-83, 1998.

Widegren et al., "The Structure and Phylogeny of a New Family of Human Endogenous Retroviruses," *J. General Virol.*, vol. 77:1631-1641, 1996.

Yu et al., "The long terminal repeat (LTR) of ERV-9 human endogenous retrovirus binds to NF-Y in the assembly of an active LTR enhancer complex NF-Y/MZF1/GATA-2," *J. Bio. Chem.*, vol. 280(42):35184-35194, 2005.

Xu et al., "A Novel Function of RNAs Arising From the Long Terminal Repeat of Human Endogenous Retrovirus 9 in Cell Cycle Arrest," *J Virol* 87(1):25-36, 2013.

\* cited by examiner

Human Primary Keratinocytes

Human Primary Lymphocytes

HT1080 cells

MDA-231 cells

OLIGONUCLEOTIDES OF HUMAN ENDOGENOUS RETROVIRUS 9 (ERV-9) LONG TERMINAL REPEAT (LTR) AND METHODS OF USE

CROSS REFERENCE TO RELATED APPLICATIONS

This is the U.S. National Stage of International Application No. PCT/US2009/056722, filed Sep. 11, 2009, which was published in English under PCT Article 21(2), which in turn claims the benefit of U.S. Provisional Application No. 61/191,911, filed Sep. 11, 2008, which is incorporated herein in its entirety.

FIELD

This disclosure concerns oligonucleotides specific for ERV-9 LTR and methods of their use for treating human diseases, such as cancer.

BACKGROUND

Human endogenous retroviruses (HERVs) are remnants of retroviruses that integrated into the human genome 6-15 million years ago and have remained an integral part of the genome throughout evolution. One significant type of HERV is ERV-9; approximately 5% of the total human genome comprises sequences from this retrovirus family of 30-40 members (Costas and Naveira, *Mol. Biol. Evol.* 17(2):320-330, 2000). The human genome contains approximately 50 copies of ERV-9 along with 3000-4000 copies of solitary elements of ERV-9 regulatory regions, called long terminal repeats (LTRs) (Pi et al., *Proc. Natl. Acad. Sci.* 101(3):805-810, 2004).

Solitary LTRs include U3, R and U5 regions, but do not contain any viral genes. U3 contains promoter and enhancer elements that drive expression of genes located proximally to the LTR. In addition, the U3 enhancer contains 14 tandemly repeated subunits with recurrent motifs. The 5' end of the R region marks the initiation site of retroviral RNA synthesis. The U5 region is also transcribed (Pi et al., *Proc. Natl. Acad. Sci.* 101(3):805-810, 2004).

During primate evolution, HERV LTRs were self-replicated and inserted into various chromosomal sites. HERV LTR sequences were once thought to be merely selfish DNA with no relevant cellular function. However, some studies suggest that the enhancer and promoter elements in the U3 region of HERV LTRs initiate and promote transcription of host genes located immediately downstream of the LTRs. ERV-9 LTR sequences have been identified in proximity to several human genes, including the β-globin locus control region (β-LCR) (Ling et al., *J. Virol.* 76(5):2410-2423, 2002), the embryonic axin gene (Ling et al., *J. Virol.* 76(5):2410-2423, 2002) and ZNF80 (Di Cristofano et al., *Nucleic Acids Res.* 23(15):2823-2830, 1995). The ability of HERV LTR sequences to enhance expression of proximal genes can result in upregulation of genes that contribute to diseases such as cancer. Thus, a need exists to inhibit HERV enhancer activity.

SUMMARY

It is disclosed herein that oligonucleotides that target the human endogenous retrovirus-9 (ERV-9) long terminal repeat (LTR) inhibit proliferation of a wide variety of cancer cell types. Both sense and antisense oligonucleotides that specifically hybridize with ERV-9 LTR nucleic acid sequences exhibit these inhibitory properties.

Provided herein is a method of treating a subject having a disease or disorder associated with expression of ERV-9 RNA (such as a tumor or cancer), comprising selecting a subject in need of treatment (for example, by detecting expression of ERV-9 RNA in a sample from the subject, such as a tumor sample) and administering to the subject a therapeutically effective amount of at least one oligonucleotide targeting an ERV-9 LTR. In some examples, the oligonucleotide(s) target the U3 region of the ERV-9 LTR. In other examples, the oligonucleotide(s) target the U5 region of the ERV-9 LTR. In particular examples, the oligonucleotide(s) are small interfering RNA (siRNA), for example, an siRNA that targets the U3 region of the ERV-9 LTR.

In some embodiments, the disease or disorder that is associated with expression of ERV-9 RNA is a malignant tumor, such as a breast, prostate, liver, or fibrosarcoma tumor, or is a myeloid cancer. In other embodiments, the disease or disorder that is associated with expression of ERV-9 is a tumor (for example, a benign tumor or a malignant tumor).

Also provided are oligonucleotides that target the ERV-9 LTR. In some embodiments, the oligonucleotide is an antisense oligonucleotide that specifically hybridizes with at least a portion of the coding strand of the ERV-9 LTR. In other embodiments, the oligonucleotide is a sense oligonucleotide that specifically hybridizes with at least a portion of the non-coding strand of the ERV-9 LTR. In some embodiments, the oligonucleotide specifically hybridizes with at least a portion of the coding strand or non-coding strand of the LTR U3 region. In other embodiments, the oligonucleotide specifically hybridizes with a least a portion of the coding strand or non-coding strand of the LTR U5 region. Also provided herein are compositions comprising at least one oligonucleotide that targets the U3 region of the ERV-9 LTR.

A method of detecting ERV-9 RNA in a sample, comprising contacting the sample with an ERV-9 LTR oligonucleotide, is also provided herein. In some embodiments, the sample is a sample obtained from a subject diagnosed with cancer (for example, a malignant tumor or hematological malignancy).

Also provided is a method of diagnosing a subject with a disease or disorder (such as cancer) susceptible to treatment with an ERV-9 LTR oligonucleotide, including correlating expression of ERV-9 LTR RNA to the disease or disorder. Examples of such a method involve obtaining a sample (such as a tumor sample) from a test subject diagnosed with the disease or disorder, detecting expression of ERV-9 LTR RNA in the test sample, and comparing the expression of ERV-9 LTR RNA in the sample to a control sample, wherein an increase in expression of ERV-9 LTR RNA in the test sample from the subject, relative to expression of ERV-9 LTR RNA in the control sample, indicates that the disease or disorder is susceptible to treatment with an ERV-9 LTR oligonucleotide. In some examples, an increase in expression of the coding strand or non-coding strand of the U3 region of ERV-9 LTR indicates the subject has a disease or disorder susceptible to treatment with an ERV-9 LTR oligonucleotide. In some embodiments, the disease or disorder is cancer, for example, such as a breast, prostate, liver, or fibrosarcoma tumor, or a myeloid cancer.

The foregoing and other features and advantages will become more apparent from the following detailed description of several embodiments, which proceeds with reference to the accompanying figures.

SEQUENCE LISTING

Figure 1:
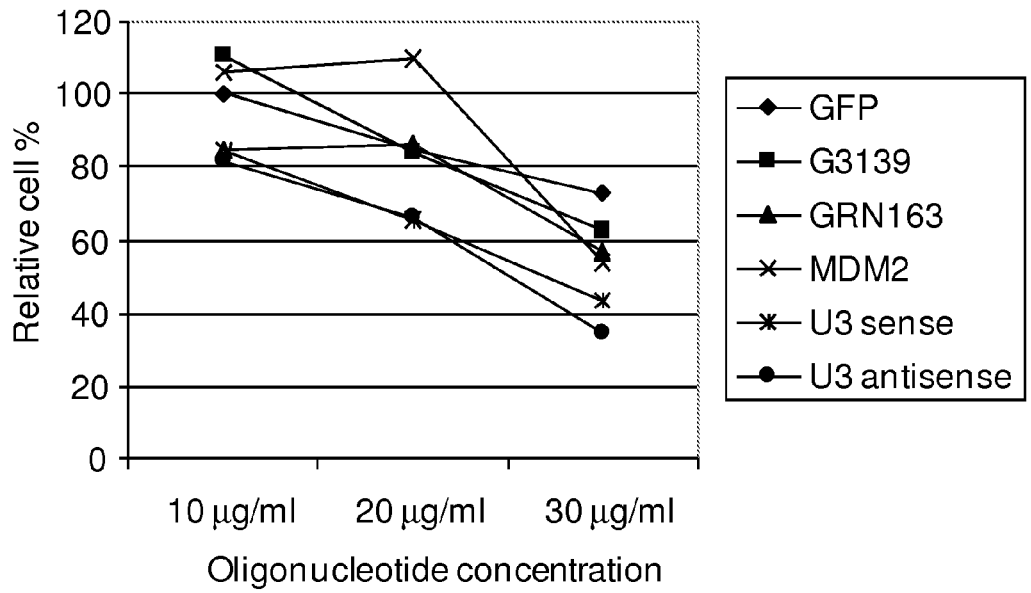
FIG. 1 is a graph showing the effect of sense and antisense ERV-9 U3 oligonucleotides (SEQ ID NOs: 1 and 2, respectively) on proliferation of HT1080 cells (a fibrosarcoma cell line). Cells ($4 \times 10^4$) were treated with ERV-9 U3 sense or antisense oligonucleotide formulated in LIPOFECTAMINE™ at the concentrations shown for 48 hours. Green fluorescent protein (GFP) sense oligonucleotide (SEQ ID NO: 3) was used as a control to measure the non-specific cytotoxicity of phosphorothioate-based oligonucleotides. Antisense oligonucleotides specific for Bcl-2 (G3139; SEQ ID NO: 4), telomerase (GRN163; SEQ ID NO: 5) and MDM2 (SEQ ID NO: 6) were also evaluated. Cell proliferation levels were expressed relative to cells transfected with 10 µg/ml GFP oligonucleotide. Both ERV-9 U3 sense and antisense oligonucleotides inhibited cell proliferation better than GFP oligonucleotide at a concentration of 10 µg/ml ($P<0.05$), and inhibited cell proliferation better than GFP control and G3139, GRN163 and MDM2 antisense oligonucleotides at concentrations of 20 µg/ml and 30 µg/ml ($P<0.05$).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 2, 2011, 18.4 KB, which is incorporated by reference herein. In the accompanying sequence listing:

SEQ ID NO: 1 is the nucleotide sequence of an ERV-9 U3 sense oligonucleotide (U3S).

SEQ ID NO: 2 is the nucleotide sequence of an ERV-9 U3 antisense oligonucleotide (U3AS).

SEQ ID NO: 3 is the nucleotide sequence of a green fluorescent protein oligonucleotide.

SEQ ID NO: 4 is the nucleotide sequence of a Bcl-2 oligonucleotide (G3139).

SEQ ID NO: 5 is the nucleotide sequence of a telomerase oligonucleotide (GRN163).

SEQ ID NO: 6 is the nucleotide sequence of an MDM2 oligonucleotide.

SEQ ID NO: 7 is the nucleotide sequence of an ERV-9 U3 sense oligonucleotide (U3S4).

SEQ ID NO: 8 is the nucleotide sequence of an ERV-9 U3 antisense oligonucleotide (U3AS4).

SEQ ID NO: 9 is the nucleotide sequence of an ERV-9 U3 sense oligonucleotide (U3S5).

SEQ ID NO: 10 is the nucleotide sequence of an ERV-9 U3 antisense oligonucleotide (U3AS5).

SEQ ID NO: 11 is the nucleotide sequence of an ERV-9 U5 sense oligonucleotide (U5S).

SEQ ID NO: 12 is the nucleotide sequence of an ERV-9 U5 antisense oligonucleotide (U5AS).

SEQ ID NOs: 13 and 14 are the nucleotide sequences of ERV-9 U3 siRNA oligonucleotides.

SEQ ID NOs: 15-17 are the nucleotide sequences of ribonucleotide reductase subunit M2 (RRM2) siRNA oligonucleotides.

SEQ ID NO: 18 is the nucleotide sequence of the ZNF80-linked ERV-9 LTR (deposited under GenBank Accession No. X83497 on Dec. 21, 1994). The ERV-9 LTR corresponds to nucleotides 80-1788.

SEQ ID NO: 19 is the nucleotide sequence of the β-globin locus control region containing the ERV-9 LTR (deposited under GenBank Accession No. AF064190 on Feb. 10, 1999). The ERV-9 LTR corresponds to nucleotides 2660-4349.

SEQ ID NO: 20 is the nucleotide sequence of a human ERV-9 retrotransposon LTR (deposited under GenBank Accession No. AF064191 on Feb. 10, 1999).

SEQ ID NOs: 21 and 22 are the nucleotide sequences of primers used to detect ERV-9 RNAs.

DETAILED DESCRIPTION

I. Abbreviations

| | |
|---|---|
| AS | antisense |
| DNA | deoxyribonucleic acid |
| ERV | endogenous retrovirus |
| GFP | green fluorescent protein |
| HERV | human endogenous retrovirus |
| LTR | long terminal repeat |
| miRNA | microRNA |
| mRNA | messenger RNA |
| RNA | ribonucleic acid |
| RNAi | RNA interference |
| RT-PCR | reverse transcriptase polymerase chain reaction |
| shRNA | short hairpin RNA |
| siRNA | small interfering RNA |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Administration: The introduction of a composition into a subject by a chosen route. For example, if the chosen route is intravenous, the composition is administered by introducing the composition into a vein of the subject.

Antisense compound: Refers to an oligomeric compound (such as an oligonucleotide) that is at least partially complementary to the region of a target nucleic acid molecule to which it hybridizes. In some embodiments, an antisense compound is an oligonucleotide that hybridizes with the coding strand of a target nucleic acid molecule, which oligonucleotide is referred to herein as an "antisense oligonucleotide." In other embodiments, an antisense compound is an oligonucleotide that hybridizes with the non-coding strand of a target nucleic acid molecule, which oligonucleotide is referred to herein as a "sense oligonucleotide." In other words, an antisense oligonucleotide comprises a sequence that is complementary to the coding strand of a target nucleic acid molecule and a sense oligonucleotide comprises a sequence that is complementary to the non-coding strand of a target nucleic acid molecule.

As used herein, an antisense compound or oligonucleotide that is "specific for" a target nucleic acid molecule is one that specifically hybridizes with and modulates expression of the target nucleic acid molecule. As used herein, a "target" nucleic acid molecule is a nucleic acid molecule to which an antisense compound is designed to specifically hybridize and modulate expression. In some embodiments, the target nucleic acid molecule is the ERV-9 LTR, for example the U3 region or the U5 region of the LTR. Non-limiting examples of antisense compounds include oligonucleotides, primers, probes, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Antisense and sense oligonucleotides: As used herein, "antisense oligonucleotide" and "sense oligonucleotide" refer to single-stranded oligomeric compounds. An antisense or sense oligonucleotide can include one or more chemical modifications to the sugar, base, and/or internucleoside linkages. Generally, antisense and sense oligonucleotides are "DNA-like" such that when the oligonucleotide hybridizes to a target mRNA, the duplex is recognized by RNase H (an enzyme that recognizes DNA:RNA duplexes), resulting in cleavage of the mRNA.

Bcl-2: An anti-apoptotic (inhibitor of cell death) protein that has been associated with the development of a variety of different types of cancer. Bcl-2 is the target of some cancer therapies, including GENASENSE™ (G3139; SEQ ID NO: 4), an antisense oligonucleotide specific for Bcl-2.

Cancer, neoplasia, malignancy or tumor: The result of abnormal and uncontrolled growth of cells. Neoplasia, malignancy, cancer and tumor are often used interchangeably and refer to abnormal growth of a tissue or cells that results from excessive cell division. The term "tumor" as used herein encompasses solid tumors (such as a benign tumor or a malignant tumor) and hematological malignancies.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological malignancies (hematological tumors) include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

In some embodiments, a malignant tumor includes, but is not limited to, breast cancer, liver cancer, prostate cancer, fibrosarcoma and myeloid cancer. As used herein, "malignant tumor" is interchangeable with "cancer."

Chemotherapeutic agent: An agent with therapeutic usefulness in the treatment of diseases characterized by abnormal cell growth or hyperplasia. Such diseases include cancer, autoimmune disease as well as diseases characterized by hyperplastic growth, such as psoriasis. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* $2^{nd}$ ed., ©2000 Churchill Livingstone, Inc; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993). Classes of chemotherapeutic agents include, but are not limited to, alkylating agents, anti-metabolites, taxanes, topoisomerase inhibitors, tumor-specific monoclonal antibodies, or hormone receptor inhibitors.

Coding and non-coding strands: A coding strand of a nucleic acid molecule has the same base sequence as its corresponding mRNA transcript (with the exception that "T" is replaced with "U"). A coding strand can also be referred to as a "sense strand" or "non-template strand." A non-coding strand of a nucleic acid molecule is complementary to the coding strand and can also be referred to as the "template strand," "anti-coding strand," or "antisense strand." One of ordinary skill in the art will recognize that an antisense oligonucleotide that specifically hybridizes with the coding strand of a target nucleic acid molecule is also capable of hybridization with a nucleic acid complementary to the non-coding strand of the nucleic acid molecule. Similarly, a sense oligonucleotide that specifically hybridizes with the non-coding strand of a target nucleic acid molecule is also capable of hybridization with a nucleic acid complementary to the coding strand of the nucleic acid molecule.

Contacting: As used herein, "contacting" includes incubating two or more compounds (such as an oligonucleotide and isolated RNA) in an appropriate medium (such as PBS or other solution) to allow for physical interaction of the two compounds.

Disease or disorder associated with ERV-9 RNA: Refers to any pathological condition in which ERV-9 RNA (for example, ERV-9 coding (sense) or non-coding (antisense) RNA) is expressed, or is more abundantly expressed than in the absence of the pathological condition.

Endogenous retrovirus: Retroviruses that integrated into the genome of humans (and other primates) millions of years ago and persist in the human genome (or genome of other primates).

Human endogenous retrovirus 9 (ERV-9): ERV-9 refers to a family of human endogenous retroviruses that contains approximately 30-50 members. ERV-9 retrovirus sequences comprise a significant (approximately 5%) portion of the human genome (see Costas and Naveira, *Mol. Biol. Evol.* 17(2):320-330, 2000, herein incorporated by reference).

ERV-9 RNA: Includes any RNA molecule transcribed from either the coding or non-coding strand of an ERV-9 nucleic acid sequence. ERV-9 RNAs can include non-ERV-9 sequence, such as sequence from a proximal gene.

Hybridization: Oligonucleotides and their analogs hybridize by hydrogen bonding, which includes Watson-Crick, Hoogsteen or reversed Hoogsteen hydrogen bonding, between complementary bases. Generally, nucleic acids consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid molecules or two distinct regions of the same nucleic acid molecule.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acids. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, 4$^{th}$ ed., John Wiley & Sons, Inc., 1999.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Isolated: An "isolated" biological component (such as a nucleic acid molecule, protein or organelle) has been substantially separated or purified away from other biological components of the cell or the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins.

Label: A detectable compound or composition that is conjugated directly or indirectly to another molecule (such as an oligonucleotide) to facilitate detection of that molecule. Specific, non-limiting examples of labels include fluorescent molecules, enzymatic linkages and radioactive isotopes.

Long terminal repeat (LTR): Retrovirus genomes comprise LTRs flanking functional genes (such as the gag, pol and env genes). Retroviruses have two LTRs, one at the 5' end and one at the 3' end of the viral genome. The LTRs mediate integration of the retroviral DNA into the host cell genome. LTRs also contain an active RNA polymerase II promoter which allows transcription of the integrated provirus by host cell RNA polymerase II to generate new copies of the retroviral genome. Regions within the LTR are designated U3, R and U5. The U3 region contains the promoter and enhancer elements, which can enhance expression of genes located proximally to the LTR. The U3 enhancer contains 14 tandemly repeated subunits with recurrent motifs. The 5' end of the R region marks the initiation site of retroviral RNA synthesis. The U5 region is also transcribed (Pi et al., *Proc. Natl. Acad. Sci.* 101(3):805-810, 2004).

MDM2: A protein that functions as a negative regulator of the tumor suppressor p53. MDM2 is overexpressed in a number of different types of tumors and has been associated with poor prognosis in a variety of human malignancies.

MicroRNA (miRNA): Single-stranded RNA molecules that regulate gene expression. miRNAs are generally 21-23 nucleotides in length. miRNAs are processed from primary transcripts known as pri-miRNA to short stem-loop structures called pre-miRNA and finally to functional miRNA. Mature miRNA molecules are partially complementary to one or more messenger RNA molecules, and their primary function is to down-regulate gene expression. MicroRNAs regulate gene expression through the RNAi pathway.

Modification: As used herein, "modification" of an oligonucleotide refers to any type of chemical change to the oligonucleotide that differs from the natural form of the oligonucleotide. For example, oligonucleotide modifications, include but are not limited to, internucleoside linkage modifications, sugar modifications and base modifications.

Nucleotide: Nucleotides include, but are not limited to, monomers that include a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of nucleotides joined by internucleoside linkages, usually between about 6 and about 100 nucleotides in length. An oligonucleotide analog refers to moieties that function similarly to oligonucleotides but have non-naturally occurring portions. For example, oligonucleotide analogs can contain non-naturally occurring portions, such as altered sugar moieties, bases or internucleoside linkages. As used herein, an "ERV-9 LTR oligonucleotide" is an oligonucleotide that specifically hybridizes with the coding strand or non-coding strand of the ERV-9 LTR. Similarly, "ERV-9 U3 oligonucleotide" and "ERV-9 U5 oligonucleotide" refer to oligonucleotides that specifically hybridize with a nucleic acid sequence of the ERV-9 U3 region or the ERV-9 U5 region, respectively. In the context of the current disclosure, ERV-9 U3 and ERV-9 U5 oligonucleotides are encompassed by ERV-9 LTR oligonucleotides.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term purified does not require absolute purity; rather, it is intended as a relative term. Thus, for example, a purified cell, protein or nucleic acid is one in which the specified cell, protein or nucleic acid is more enriched than it is in its generative environment, for instance within a cell or organism. Preferably, a preparation of a specified cell, protein or nucleic acid is purified such that it represents at least 50% of the total content of the preparation. In some embodiments, a purified preparation contains at least 60%, at least 70%, at least 80%, at least 85%, at least 90%, at least 95% or more of the specified cell, protein or nucleic acid.

Ribozyme: A catalytic RNA molecule. In some cases, ribozymes can bind to specific sites on other RNA molecules and catalyze the hydrolysis of phosphodiester bonds in the RNA molecules.

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs.

Sample: As used herein, a "sample" obtained from a subject refers to a cell, fluid or tissue sample. Bodily fluids include, but are not limited to, blood, serum, urine, saliva, sputum and spinal fluid. Tissues include those from biopsies, autopsies and pathology specimens, as well as biopsied or surgically removed tissue, including tissues that are unfixed, frozen, fixed in formalin and/or embedded in paraffin.

Sequence identity: The similarity between amino acid or nucleic acid sequences. Sequence identity is frequently measured in terms of percent identity (or similarity or homology); the higher the percentage, the more similar the two sequences are. Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Res.* 16:10881-10890, 1988; Pearson and Lipman, *Proc. Natl. Acad. Sci. USA* 85:2444, 1988; and Altschul et al., *Nature Genet.* 6:119-129, 1994. The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Short hairpin RNA (shRNA): An RNA that makes a tight hairpin turn and can be used to silence gene expression via the RNAi pathway. The shRNA hairpin structure is cleaved by the cellular machinery into siRNA.

Small interfering RNA (siRNA): A double-stranded nucleic acid molecule that modulates gene expression through the RNAi pathway. siRNA molecules are generally 20-30 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs."

Subject: Living multi-cellular vertebrate organisms, a category that includes both human and non-human mammals.

Targeting: As used herein, an oligonucleotide "targeting" a specific nucleic acid molecule refers to an oligonucleotide that is designed to specifically hybridize and modulate expression of the nucleic acid molecule.

Telomerase: A telomere-specific DNA polymerase involved in the maintenance of human chromosomes. Telomerase is a reverse transcriptase that adds specific DNA sequence repeats to the 3' end of DNA strands in the telomere regions found at the ends of eukaryotic chromosomes. Telomerase activity can be detected in a number of tumor cells, but is typically not active in normal cells.

Therapeutic agent: A chemical compound or composition capable of inducing a desired therapeutic or prophylactic effect when properly administered to a subject or a cell. Also referred to as a "pharmaceutical agent."

Therapeutically effective amount: A quantity of a specified pharmaceutical agent sufficient to achieve a desired effect in a subject, or in a cell, being treated with the pharmaceutical agent. For example, this can be the amount of an ERV-9 LTR-specific oligonucleotide required to inhibit proliferation of cancer cells or tumor growth.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

It is disclosed herein that oligonucleotides that target the LTR of ERV-9 inhibit proliferation of a number of different types of cancer cells. The oligonucleotides specifically hybridize with either the non-coding strand or the coding strand of ERV-9. The oligonucleotides described herein can be used, for example, for therapeutic purposes, such as for the treatment of cancer.

Provided herein are oligonucleotides targeting a human endogenous retrovirus (ERV)-9. In some embodiments, the oligonucleotide specifically hybridizes with the coding strand of the ERV-9 long terminal repeat (LTR). An oligonucleotide that specifically hybridizes with the coding strand of the ERV-9 LTR is referred to herein as an antisense oligonucleotide. In other embodiments, the oligonucleotide specifically hybridizes with the non-coding strand of the ERV-9 LTR. An oligonucleotide that specifically hybridizes with the non-coding strand of the ERV-9 LTR is referred herein as a sense oligonucleotide. One of ordinary skill in the art would recognize that an antisense oligonucleotide that specifically hybridizes with the coding strand of an ERV-9 LTR is also capable of hybridization with an ERV-9 LTR nucleic acid complementary to the non-coding strand. Similarly, a sense oligonucleotide that specifically hybridizes with the non-coding strand of an ERV-9 LTR is also capable of hybridization with an ERV-9 LTR nucleic acid complementary to the coding strand. In particular embodiments, the ERV-9 oligonucleotide specifically hybridizes with a nucleic acid sequence of the LTR U3 region (referred to herein as an ERV-9 U3 oligonucleotide). In other embodiments, the ERV-9 oligonucleotide specifically hybridizes with a nucleic acid sequence of the LTR U5 region (referred to herein as an ERV-9 U5 oligonucleotide).

In some examples, the nucleotide sequence of the coding strand of the ERV-9 LTR is at least about 75%, at least about 80%, at least about 85%, at least about 90%, at least about 95% or at least about 99% identical to nucleotides 80-1788 of SEQ ID NO: 18. In other examples, the nucleotide sequence of the coding strand of the ERV-9 LTR is at least about 75%, at least about 80%, at least about 85%, at least about 90%, at least about 95% or at least about 99% identical to nucleotides 2660-4349 of SEQ ID NO: 19. In other examples, the nucleotide sequence of the coding strand of the ERV-9 LTR is at least about 75%, at least about 80%, at least about 85%, at least about 90%, at least about 95% or at least about 99% identical to SEQ ID NO: 20.

In some examples, the nucleotide sequence of the non-coding strand of the ERV-9 LTR is at least about 75%, at least about 80%, at least about 85%, at least about 90%, at least about 95% or at least about 99% identical to the complement of nucleotides 80-1788 of SEQ ID NO: 18. In other examples, the nucleotide sequence of the non-coding strand of the ERV-9 LTR is at least about 75%, at least about 80%, at least about 85%, at least about 90%, at least about 95% or at least about 99% identical to the complement of the complement of nucleotides 2660-4349 of SEQ ID NO: 19. In other examples, the nucleotide sequence of the coding strand of the ERV-9 LTR is at least about 75%, at least about 80%, at least about 85%, at least about 90%, at least about 95% or at least about 99% identical to the complement of SEQ ID NO: 20.

Additional ERV-9 LTR sequences are known in the art and can be used to design sense or antisense oligonucleotides that specifically hybridize with ERV-9 LTR nucleic acid sequences. The ERV-9 LTR sense and antisense oligonucleotides need not be 100% complementary to an ERV-9 LTR sequence. The oligonucleotides contemplated herein have a sufficient degree of complementarity to hybridize with an ERV-9 LTR nucleic acid sequence and inhibit its function, such as via degradation of an ERV-9 RNA.

In some embodiments, the nucleotide sequence of the ERV-9 U3 oligonucleotide is at least about 75%, at least about 80%, at least about 85%, at least about 90%, at least about 95% or at least about 99% identical to SEQ ID NO: 1. In other embodiments, the nucleotide sequence of the ERV-9 U3 oligonucleotide is at least about 75%, at least about 80%, at least about 85%, at least about 90%, at least about 95% or at least about 99% identical to SEQ ID NO: 2. In some embodiments, the ERV-9 U3 oligonucleotide comprises the nucleotide sequence of SEQ ID NO: 1 or SEQ ID NO: 2. In some examples, the ERV-9 U3 oligonucleotide consists of SEQ ID NO: 1. In other examples, the ERV-9 U3 oligonucleotide consists of SEQ ID NO: 2.

In other embodiments, the nucleotide sequence of the ERV-9 U3 oligonucleotide is at least about 75%, at least about 80%, at least about 85%, at least about 90%, at least about 95% or at least about 99% identical to SEQ ID NO: 7, SEQ ID NO: 8, SEQ ID NO: 9, or SEQ ID NO: 10. In some embodiments, the ERV-9 U3 oligonucleotide comprises the nucleotide sequence of SEQ ID NO: 7, SEQ ID NO: 8, SEQ ID NO: 9, or SEQ ID NO: 10. In some examples, the ERV-9 U3 oligonucleotide consists of SEQ ID NO: 7. In other examples, the ERV-9 U3 oligonucleotide consists of SEQ ID NO: 8. In other examples, the ERV-9 U3 oligonucleotide consists of SEQ ID NO: 9. In other examples, the ERV-9 U3 oligonucleotide consists of SEQ ID NO: 10.

In some embodiments, the nucleotide sequence of the ERV-9 U5 oligonucleotide is at least about 75%, at least about 80%, at least about 85%, at least about 90%, at least about 95% or at least about 99% identical to SEQ ID NO: 11 or SEQ ID NO: 12. In some embodiments, the ERV-9 U5 oligonucleotide comprises the nucleotide sequence of SEQ ID NO: 11 or SEQ ID NO: 12. In some examples, the ERV-9 U5 oligonucleotide consists of SEQ ID NO: 11 or SEQ ID NO: 12.

The ERV-9 LTR oligonucleotides can be single-stranded, double-stranded or comprise partial double-stranded structure, such as a hairpin. In some examples, the sense and antisense oligonucleotides are single-stranded. In other examples, the sense and antisense oligonucleotides are double-stranded, such as an siRNA molecule (for example, an siRNA that targets the U3 region of the ERV-9 LTR). In a particular embodiment, the siRNA is a double stranded ERV-9 U3 oligonucleotide in which one strand is at least about 75%, at least about 80%, at least about 85%, at least about 90%, at least about 95% or at least about 99% identical to SEQ ID NO: 13 and the other strand is at least about 75%, at least about 80%, at least about 85%, at least about 90%, at least about 95% or at least about 99% identical to SEQ ID NO: 14. In some embodiments, the ERV-9 U3 siRNA comprises the nucleotide sequence of SEQ ID NO: 13 and SEQ ID NO: 14. In some examples, the ERV-9 U3 siRNA consists of SEQ ID NO: 13 and SEQ ID NO: 14.

The length of an ERV-9 LTR oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the ERV-U3 oligonucleotides are about 20 to about 35 nucleotides in length. In some embodiments, the ERV-U3 oligonucleotides are about 22 to about 28 nucleotides in length. In some embodiments, the ERV-U3 oligonucleotides are about 22, about 24, about 26 or about 27 nucleotides in length.

The ERV-9 LTR oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. In some embodiments, the oligonucleotides comprise at least one modified internucleoside linkage. In some embodiments, the oligonucleotides comprise modified internucleoside linkages at each position. In some embodiments, the oligonucleotides comprise at least one modified sugar moiety. In some embodiments, the oligonucleotides comprise modified sugar moieties at each position. In some embodiments, the oligonucleotides comprise at least one modified base. In some embodiments, the oligonucleotides comprise modified bases at each position. In some embodiments, the oligonucleotides comprise at least one modified internucleoside linkage, at least one modified sugar moiety, and at least one modified base.

In some examples, the modified internucleoside linkage is a phosphorothioate linkage. In some examples, the sugar modification is selected from 2'-fluoro, 2'-O-methyl and 2'-methoxyethoxy. In some examples, the modified base is 5-methylcytosine.

Also provided herein are compositions comprising one or more of the ERV-9 LTR oligonucleotides disclosed herein. In some embodiments, the compositions comprise a pharmaceutically acceptable carrier. In some embodiments, the compositions comprise additional therapeutic agents, such as other oligonucleotides or a chemotherapeutic agent.

Further provided herein is a method of treating a subject having a disease or disorder associated with expression of ERV-9 LTR RNA (such as a tumor or cancer). In some embodiments, the method comprises selecting a subject in need of treatment and administering to the subject a therapeutically effective amount of a first therapeutic agent, wherein the first therapeutic agent comprises at least one oligonucleotide targeting an ERV-9 LTR, as disclosed herein. Also provided is a method of treating a subject having a disease or disorder associated with expression of ERV-9 RNA, comprising selecting a subject in need of treatment and administering to the subject a therapeutically effective amount of a first therapeutic agent, wherein the first therapeutic agent comprises a composition comprising an oligonucleotide targeting an ERV-9 LTR. In some embodiments, two or more ERV-9 LTR oligonucleotides are administered to the subject. In some examples, an ERV-9 LTR sense oligonucleotide and an ERV-9 LTR antisense oligonucleotide are administered to the subject. In other examples, two or more ERV-9 LTR sense oligonucleotides are administered to the subject. In other examples, two or more ERV-9 LTR antisense oligonucleotides are administered to the subject. In still further examples, at least one ERV-9 LTR siRNA is administered to the subject.

The subject can be any subject that would benefit from treatment with an ERV-9 LTR oligonucleotide disclosed herein. For example, the subject can be a subject diagnosed with a hyperproliferative disorder that is at least in part associated with abnormal expression of ERV-9 RNAs. In some embodiments, the hyperproliferative disorder is cancer (for example, a malignant tumor or a hematological malignancy). In some examples, the malignant tumor is breast cancer, liver cancer, prostate cancer, or fibrosarcoma. In some examples, the cancer is a myeloid cancer, for example, myelogenous leukemia, such as acute myeloid leukemia or chronic myeloid leukemia. In other examples, the hyperproliferative disorder includes a tumor (for example, a benign tumor or a malignant tumor).

In particular examples, the subject in need of treatment with an ERV-9 LTR oligonucleotide is selected by determining that a cancer expresses a coding strand or a non-coding strand of an ERV-9 LTR (for example, the U3 region of the ERV-9 LTR). In a particular example, the subject is selected for treatment with an ERV-9 LTR oligonucleotide by obtaining a sample from a test subject diagnosed with the disease or disorder, detecting expression of the coding strand or the non-coding strand of the ERV-9 LTR RNA in the test sample (such as a tumor sample), and comparing the expression of the coding strand or the non-coding strand of the ERV-9 LTR RNA in the test sample to a control sample, wherein an increase in expression of the coding strand or the non-coding strand of the ERV-9 LTR RNA in the test sample, relative to expression of the coding strand or the non-coding strand of the ERV-9 LTR RNA in the control sample (such as at least about a 20% increase, for example, at least about a 30%, 40%, 50%, 60%, 70%, 80%, 90%, 100%, 150%, 200%, or more increase) indicates that the subject is in need of treatment with an ERV-9 LTR oligonucleotide. In particular embodiments, an increase in the expression of the ERV-9 LTR U3 region coding strand in the sample from the subject relative to the control sample indicates a subject for treatment with an ERV-9 LTR oligonucleotide.

In some embodiments, the control is a sample obtained from a healthy patient or a non-cancerous tissue sample obtained from the patient diagnosed with cancer (such as a matched non-cancerous sample from the same tissue as the cancer). In other embodiments, the control is a historical control or standard reference value or range of values (such as a previously tested control sample, such as a group of samples that represent baseline or normal values, such as the level of ERV-9 LTR in non-cancerous tissue).

Also provided herein is a method of treating a subject having a disease or disorder (such as a tumor or cancer) associated with expression of ERV-9 RNA, comprising selecting a subject in need of treatment, administering to the subject a therapeutically effective amount of a first therapeutic agent, wherein the first therapeutic agent is at least one oligonucleotide targeting an ERV-9 LTR, and further administrating a second therapeutic agent. In some embodiments, the second therapeutic agent is an antisense compound, such as an antisense oligonucleotide, siRNA, miRNA, shRNA or ribozyme. In some embodiments, the antisense compound is an antisense oligonucleotide that specifically targets a nucleic acid associated with the development or progression of cancer. In some examples, the antisense oligonucleotide is specific for Bcl-2, telomerase, or MDM2.

In other embodiments, the second therapeutic agent is a chemotherapeutic agent. The chemotherapeutic agent can be any type of chemotherapeutic agent used in the treatment of cancer. In some embodiments, the chemotherapeutic agent is an alkylating agent, anti-metabolite, taxane, topoisomerase inhibitor, tumor-specific monoclonal antibody, or hormone receptor inhibitor. In some examples, the chemotherapeutic agent is etoposide, cisplatin, taxol, finasteride, or tamoxifen.

In additional embodiments, the second therapeutic agent is radiation, for example, radiation therapy. In particular examples, radiation therapy includes external beam therapy (for example, delivery of a beam of high-energy x-rays to the location of the tumor). In other examples, radiation therapy includes intensity-modulated radiation therapy (IMRT), which is able to focus more precisely so that fewer healthy cells are destroyed than is the case with external beam therapy. IMRT reduces incidental damage to the structures near the tumor that may not be involved. In further examples, radiation therapy includes total body irradiation. Methods and therapeutic dosages of radiation therapy are known to those skilled in the art, and can be determined by a skilled clinician.

The first and second therapeutic agents can be delivered at the same time, for example, as part of the same composition or as separate compositions, or can be administered at different times. When administered at different times, the second therapeutic agent can either be administered before the ERV-9 LTR oligonucleotide or after the ERV-9 LTR oligonucleotide. The time between administration of the first therapeutic agent and the second therapeutic agent can vary and will depend on the type of second therapeutic agent selected, the cancer being treated, and the subject being treated. One of skill in the art can determine an appropriate dosing schedule for each subject.

In some embodiments, the ERV-9 LTR oligonucleotide is administered to a subject in a single dose. In other embodiments, the ERV-9 LTR oligonucleotide is administered to a subject in multiple doses. When administered in multiple doses, the time period between each administration can vary and will depend in part on the subject being treated and the type of cancer being treated. In some examples, the ERV-9 LTR oligonucleotide is administered multiple times per day (such as 2, 3, 4, or more times per day), daily, bi-weekly, weekly, bi-monthly or monthly. Similarly, the second therapeutic agent, if given, can be administered in a single dose or in multiple doses. When administered in multiple doses, the time period between each administration can vary and will depend in part on the subject being treated, the type of cancer being treated, and the type of therapeutic agent selected.

Also provided herein is a method of detecting expression of ERV-9 RNA in a sample. In some embodiments, the sample is a sample obtained from a subject diagnosed with a disease or disorder, for example a hyperproliferative disorder, such as cancer.

In some embodiments, the method comprises isolating RNA from the sample from the subject, contacting the isolated RNA with an ERV-9 LTR oligonucleotide provided herein; and detecting hybridization of the oligonucleotide to the isolated RNA, wherein hybridization of the oligonucleotide to the isolated RNA indicates ERV-9 RNA is expressed in the sample. In some embodiments, the sample is a tissue sample, such as a tumor tissue sample or a non-tumor tissue sample. In some embodiments, the sample is a bodily fluid sample, such as a blood sample. Methods and reagents for isolating RNA from a sample are well known in the art. In some embodiments, the oligonucleotide comprises a detectable label, such as a fluorophore or a radioisotope.

In some cases, the sample is obtained from a subject diagnosed with cancer. In some embodiments, the method of detecting ERV-9 RNA expression in a sample obtained from a subject diagnosed with cancer further comprises selecting a treatment for the subject diagnosed with cancer by detecting expression of ERV-9 RNA (such as ERV-9 LTR RNA, for example the coding strand of the U3 region of the ERV-9 LTR). In some embodiments, the treatment comprises administering to the subject a therapeutically effective amount of an ERV-9 LTR oligonucleotide. In some examples, the oligonucleotide is about 15 to about 40 nucleotides in length, and the oligonucleotide specifically hybridizes with the coding strand or the non-coding strand of the ERV-9 LTR.

Further provided is a method of diagnosing a subject with a disease or disorder (such as a tumor or cancer) susceptible to treatment with an ERV-9 LTR oligonucleotide, including correlating expression of ERV-9 RNA to the disease or disorder. In some embodiments, the method comprises obtaining a sample from a test subject diagnosed with the disease or disorder, detecting expression of ERV-9 LTR RNA in the test sample (such as a tumor sample), and comparing the expression of ERV-9 LTR RNA in the sample to a control sample, wherein an increase in expression of ERV-9 LTR RNA in the test sample, relative to expression of ERV-9 LTR RNA in the control sample indicates that the disease or disorder is susceptible to treatment with an ERV-9 LTR oligonucleotide. In some embodiments, the disease or disorder is a hyperproliferative disorder. In some examples, the hyperproliferative disorder is a tumor, such as a benign tumor or a malignant tumor. Malignant tumors, include, but are not limited to breast cancer, liver cancer, prostate cancer, fibrosarcoma and myeloid cancer. In some embodiments, detecting expression of ERV-9 RNA comprises isolating RNA from the sample; contacting the isolated RNA with an ERV-9 LTR oligonucleotide; and detecting hybridization of the oligonucleotide to the isolated RNA.

In a particular example, the subject is diagnosed with a disease or disorder (such as cancer) susceptible to treatment with an ERV-9 LTR oligonucleotide by obtaining a test sample (such as a tumor sample) from the subject, detecting expression of ERV-9 LTR RNA in the test sample, and comparing the expression of ERV-9 LTR RNA in the test sample to a control sample, wherein an increase in expression of ERV-9 LTR RNA in the test sample, relative to expression of ERV-9 LTR RNA in the control sample (such as at least about a 20% increase, for example, at least about a 30%, 40%, 50%, 60%, 70%, 80%, 90%, 100%, 150%, 200%, or more increase) indicates that the disease or disorder is susceptible to treatment with an ERV-9 LTR oligonucleotide. In particular embodiments, an increase in the expression of the ERV-9 LTR U3 region coding strand in the sample relative to the control is sufficient to diagnose the subject as having a disease or disorder (such as cancer) susceptible to treatment with an ERV-9 LTR oligonucleotide.

In some embodiments, the control is a sample obtained from a healthy patient or a non-cancerous tissue sample obtained from the patient diagnosed with cancer (such as a matched non-cancerous sample from the same tissue as the cancer). In other embodiments, the control is a historical control or standard reference value or range of values (such as a previously tested control sample, such as a group of samples that represent baseline or normal values, such as the level of ERV-9 LTR in non-cancerous tissue).

It is contemplated herein that detection of the ERV-9 RNA can be performed, for example, on tissue or bodily fluid samples obtained from a subject. In some cases, ERV-9 RNA will be detected directly in a tumor. In other cases, ERV-9 RNA expression will be detected in adjacent non-tumor tissue. For example, to correlate expression of ERV-9 RNA to liver cancer, a sample can be obtained from a liver tumor or from non-cancerous liver tissue adjacent to the tumor. In another example, to correlate ERV-9 RNA expression to a myeloid cancer, the sample can be a blood sample to detect expression in myeloid cells in the blood. If a particular type of disease or disorder (such as cancer) is associated with expression of ERV-9 RNA, this information can be used to determine an appropriate therapy for a patient diagnosed with the disease or disorder. For example, the patient having the disease or disorder can be treated with an ERV-9 LTR oligonucleotide as a means of therapy.

In some embodiments of the detection methods, the oligonucleotides comprise a detectable label, such as a fluorescent molecule, enzymatic linkage or radioisotope. Methods of detecting hybridization of nucleic acid molecules are well known in the art. Such methods include detecting a fluorescent or radioactive signal (depending on the type of detectable label used). When enzymatic labels are used, hybridization can be detected by applying the appropriate enzymatic substrate and detecting the product.

IV. Antisense Compounds

As used herein, the term "antisense compound" refers to a class of oligomer-based compounds that specifically hybridize with a target nucleic acid molecule. Oligonucleotides are one type of antisense compound. Disclosed herein are sense and antisense oligonucleotides that specifically hybridize with the non-coding and coding strands, respectively, of the ERV-9 LTR. As used herein, both ERV-9 LTR (including ERV-9 U3 and ERV-9 U5) sense and antisense oligonucleotides are antisense compounds.

Generally, the principle behind antisense technology is that an antisense compound hybridizes to a target nucleic acid and effects the modulation of gene expression activity or function, such as transcription, translation or splicing. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide. Antisense compounds can also be used to modulate gene expression, such as splicing, by occupancy-based inhibition, such as by blocking access to splice sites. As used herein, antisense compounds include, but are not limited to, "antisense oligonucleotides" and "sense oligonucleotides" that target an ERV-9 LTR sequence.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Another type of antisense compound that utilizes the RNAi pathway is a microRNA. MicroRNAs are naturally occurring RNAs involved in the regulation of gene expression. However, these compounds can be synthesized to regulate gene expression via the RNAi pathway. Similarly, shRNAs are RNA molecules that form a tight hairpin turn and can be used to silence gene expression via the RNAi pathway. The shRNA hairpin structure is cleaved by the cellular machinery into siRNA.

Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a messenger RNA.

Each of the above-described antisense compounds provides sequence-specific target gene regulation. This sequence-specificity makes antisense compounds effective tools for the selective modulation of a target nucleic acid of interest.

A. Designing Oligonucleotides Specific for the ERV-9 LTR

As taught herein, treatment of cancer cells with oligonucleotides specific for the ERV-9 LTR inhibit proliferation of the cancer cells. Thus, provided herein are sense and antisense oligonucleotides targeting the ERV-9 LTR and methods of use for treating a subject diagnosed with cancer. In some cases, the oligonucleotides target the U3 region of the LTR. In other cases, the oligonucleotides target the U5 region of the LTR. Any type of antisense compound that specifically targets and regulates expression of RNAs corresponding to the ERV-9 LTR is contemplated for use with the disclosed methods. Such antisense compounds include single-stranded compounds, such as antisense and sense oligonucleotides, and double-stranded compounds, including compounds with at least partial double-stranded structure, including siRNAs, miRNAs, shRNAs and ribozymes.

As discussed in the Examples below, it is disclosed herein that expression of both ERV-9 sense and antisense RNAs can be detected in cancer cells. Accordingly, both ERV-9 LTR sense and antisense oligonucleotides are shown to inhibit proliferation of cancer cells and tumor growth.

Methods of designing, preparing and using antisense compounds that specifically target the ERV-9 LTR (including the U3 and U5 regions of the LTR) are within the abilities of one of skill in the art (see, for example, Crook, *Ann. Rev. Pharmacol. Toxicol.* 32:329-376, 1992; Krutzfeldt et al., *Nature* 438(1):685-689, 2005, each of which is herein incorporated by reference). ERV-9 LTR antisense compounds can be designed and purchased from a variety of commercial sources, such as from Dharmacon (Lafayette, Colo.), moleculA (Columbia, Md.), Invitrogen (Carlsbad, Calif.), Integrated DNA Technologies (San Diego, Calif.), GenScript Corporation (Piscataway, N.J.) and Ambion (Austin, Tex.). In addition, siRNA design sources are available online, including siDirect from the University of Tokyo (design.rnai.jp), siRNA at Whitehead from the Whitehead Institute for Biomedical Research (jura.wi.mit.edu/bioc/siRNAext), and siRNA Design Software from the University of Hong Kong (i.cs.hku.hk/~sima/software/sirna.php).

Furthermore, nucleic acid sequences for ERV-9 are publicly available, including, but not limited to GenBank Accession No. X83497, deposited Dec. 21, 1994 (SEQ ID NO: 18); GenBank Accession No. AF064190, deposited Feb. 10, 1999 (SEQ ID NO: 19); and GenBank Accession No. AF064191, deposited Feb. 10, 1999 (SEQ ID NO: 20). Each of the sequences provided in the above-listed GenBank Accession numbers is herein incorporated by reference as present in GenBank on Sep. 11, 2008. Antisense compounds specifically targeting the ERV-9 LTR can be prepared by designing compounds that are complementary to an ERV-9 LTR nucleotide sequence, such as a coding sequence or a non-coding sequence. Antisense compounds targeting ERV-9 LTR need not be 100% complementary to ERV-9 LTR to specifically hybridize and regulate expression of the target nucleic acid.

For example, the antisense compound can be at least 75%, at least 80%, at least 85%, at least 90%, at least 95%, at least 99% or 100% complementary to the selected ERV-9 LTR nucleic acid sequence. Methods of screening antisense compounds for specificity are well known in the art (see, for example, U.S. Pre-Grant Publication No. 2003-0228689, herein incorporated by reference).

In some embodiments, the ERV-9 LTR antisense compounds described herein are sense or antisense oligonucleotides. The ERV-9 LTR oligonucleotides can be any suitable length to allow for hybridization and modulation of gene expression. The length of an ERV-9 LTR oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the ERV-9 LTR oligonucleotides are about 20 to about 35 nucleotides in length. In some embodiments, the ERV-9 LTR oligonucleotides are about 25 to about 30 nucleotides in length. In some embodiments, the ERV-9 LTR oligonucleotides are about 27 nucleotides in length.

The ERV-9 LTR oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

B. Oligonucleotide Modifications

In some examples, the antisense compounds or oligonucleotides described herein contain one or more modifications to enhance nuclease resistance and/or increase activity of the compound. Modified antisense compounds or oligonucleotides include those comprising modified backbones or non-natural internucleoside linkages. As defined herein, oligonucleotides having modified backbones include those that retain a phosphorus atom in the backbone and those that do not have a phosphorus atom in the backbone.

Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In some embodiments, both the sugar and the internucleoside linkage of the nucleotide units of the oligonucleotide or antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (*Science* 254:1497-1500, 1991).

Modified oligonucleotides can also contain one or more substituted sugar moieties. In some examples, the oligonucleotides can comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta,* 78, 486-504, 1995). In other examples, the modification includes 2'-dimethylaminooxyethoxy (also known as 2'-DMAOE) or 2'-dimethylaminoethoxyethoxy (also known in the art as 2'-O-dimethylaminoethoxyethyl or 2'-DMAEOE).

Similar modifications can also be made at other positions of the compound. Antisense compounds or oligonucleotides can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, *Antisense Research and Applications*, pages 289-302, Crooke, S. T. and Lebleu, B., ed., CRC Press, 1993).

Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

C. Delivery of Antisense Compounds

Antisense compounds can be delivered to a cell, tissue or organ using any of a number of methods well known in the art. Such methods include, but are not limited to, liposomal-mediated transfection, electroporation, and conjugation of the antisense compound to a cell-penetrating peptide (CPP). Transfection of antisense compounds generally involves the use of liposomal-mediated transfection reagents (such as LIPOFECTAMINE™), a number of which are commercially available. Methods for transfection and electroporation of nucleic acids, including antisense compounds, are well known in the art (see, for example, U.S. Pat. Nos. 7,307,069 and 7,288,530; Pretchtel et al., *J. Immunol. Methods* 311(1-2):139-52, 2006; Ghartey-Tagoe et al., *Int. J. Pharm.* 315(1-2):122-133, 2006, each of which are herein incorporated by reference). In additional examples, the antisense compounds can be delivered with a vector, such as a viral vector (for example, an adenovirus, lentivirus, or adeno-associated virus vector).

CPPs are a family of polypeptides that facilitate transduction of proteins, nucleic acids or other compounds across membranes in a receptor-independent manner (Wadia and Dowdy, *Curr. Protein Pept. Sci.* 4(2):97-104, 2003). Typically, CPPs are short polycationic sequences that can facilitate cellular uptake of compounds to which they are linked into endosomes of cells. For example, delivery of antisense compounds by covalently-linked cationic cell penetrating peptides has been previously described (Abes et al., *J. Control Release* 116(3):304-13, 2006).

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide. When fused with other proteins, the Tat peptide has been demonstrated to deliver these proteins, varying in size from 15 to 120 kDa, into cells in tissue culture (Frankel and Pabo, *Cell* 55(6):1189-93, 1988; Green and Loewenstein, *J. Gen. Microbiol.* 134(3):849-55, 1988; Vives et al., *J. Biol. Chem.* 272(25):16010-7, 1997; Yoon et al., *J. Microbiol.* 42(4):328-35, 2004; Cai et al., *Eur. J. Pharm. Sci.* 27(4):311-9, 2006).

Other CPPs include, but are not limited to, PENETRATIN™, a 16 amino acid peptide derived from the third helix of the *Drosophila* Antennapedia homeobox gene (U.S. Pat. No. 5,888,762; Derossi et al., *J. Biol. Chem.* 269:10444-10450, 1994; Schwarze et al., *Trends Pharmacol. Sci.* 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, *FASEB J.* 12:67-77, 1998; Hawiger, *Curr. Opin. Chem. Biol.* 3:89-94, 1999); peptides from the VP22 protein of herpes simplex virus (HSV) type 1 (Elliott et al., *Cell* 88:223-233, 1997); the UL-56 protein of HSV-2 (U.S. Pre-Grant Publication No. 2006/0099677); and the Vpr protein of HIV-1 (U.S. Pre-Grant Publication No. 2005/0287648). In addition, a number of artificial peptides also are known to function as CPPs, such as poly-arginine, polylysine and others (see, for example, U.S. Pre-Grant Publication Nos. 2006/0106197; 2006/0024331; 2005/0287648; and 2003/0125242; Zhibao et al., *Mol. Ther.* 2:339-347, 2000; and Laus et al. *Nature Biotechnol.* 18:1269-1272, 2000). Each of the above-listed publications is herein incorporated by reference in its entirety.

V. Administration and Use of ERV-9 LTR Oligonucleotides

The ERV-9 LTR oligonucleotides disclosed herein can be used to treat any disease or disorder caused by aberrant gene expression resulting from ERV-9 nucleic acid sequences. The disclosed ERV-9 LTR oligonucleotides can also be used to detect ERV-9 RNA in a sample, to correlate expression of ERV-9 RNA with a particular disease or disorder, or to diagnose a subject with a disease or disorder susceptible to treatment with an ERV-9 LTR oligonucleotide.

It is disclosed herein that sense and antisense oligonucleotides targeted to the ERV-9 LTR are capable of inhibiting proliferation of a variety of cancer cells and inhibiting tumor growth in vivo. Thus, provided herein are methods of treating a subject diagnosed with a disease or disorder associated with expression of ERV-9 RNA, comprising administration of one or more of the ERV-9 LTR oligonucleotides described herein. In some cases, the disease or disorder is a hyperproliferative disorder, such as a tumor, including a malignant tumor.

The subject to be treated can be any subject that would benefit from treatment with an ERV-9 LTR oligonucleotide disclosed herein. For example, the subject can be a subject diagnosed with a cancer that is at least in part associated with abnormal expression of ERV-9 LTR RNAs. In some embodiments, the cancer is a solid tumor. In some examples, the solid tumor is breast cancer, liver cancer, prostate cancer or a fibrosarcoma. In other embodiments, the cancer is a myeloid cancer. In some examples, the myeloid cancer is myelogenous leukemia, such as acute myeloid leukemia or chronic myeloid leukemia.

In some embodiments, the ERV-9 LTR oligonucleotide is administered to a subject in a single dose. In other embodiments, the ERV-9 LTR oligonucleotide is administered to a subject in multiple doses. When administered in multiple doses, the time period between each administration can vary and will depend in part on the subject being treated and the type of cancer being treated. In some examples, the ERV-9 LTR oligonucleotide is administered daily, bi-weekly, weekly, bi-monthly or monthly. In other examples, the ERV-9 LTR oligonucleotide is administered multiple times per day, for example, two times, three times, four times, or more per day.

The dose of oligonucleotide will vary from subject to subject depending on a variety of factors, including age, weight and general condition of the subject, severity and type of disease being treated, the particular oligonucleotide selected and its mode of administration. An appropriate dose can be determined by one of ordinary skill in the art using only routine experimentation.

In some embodiments, the dose of oligonucleotide is about 10 μg to about 1000 mg, about 1 mg to about 500 mg, or about 50 mg to about 100 mg. In some examples, the dose of oligonucleotide is about 50 μg, about 100 μg, about 1 mg, about 10 mg, about 50 mg, about 100 mg, about 250 mg, about 500 mg or about 1000 mg. In some embodiments, the dose of oligonucleotide is about 1.0 mg/kg to about 100 mg/kg, or about 5.0 mg/kg to about 500 mg/kg, about 10 mg/kg to about 100 mg/kg, or about 25 to about 50 mg/kg. In some examples, the dose of oligonucleotide is about 1.0 mg/kg, about 2.5 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg.

Methods of administration include, but are not limited to, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local. For example, local administration includes administration to a specific organ, such as the liver.

Antisense compounds are administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

In some cases, the antisense compound to be delivered is a shRNA, which is encoded in an expression vector, such as a viral vector or a plasmid vector. For in vitro use, the expression vector can be introduced into cells by any of a number of means well known in the art, such as, for example, by transfection or electroporation as described above. For in vivo delivery, the viral vectors can be administered to a subject using any suitable means known in the art.

In some embodiments, an oligonucleotide is administered to a subject via an oral route of administration. In some cases, non-parenteral (oral) oligonucleotide formulations result in enhanced bioavailability (a measurement of the portion of an administered drug that reaches the circulatory system) of the oligonucleotide. Oral oligonucleotide compositions can comprise one or more mucosal penetration enhancers (also known as absorption enhancers or penetration enhancers). Accordingly, some embodiments of the disclosure comprise at least one oligonucleotide in combination with at least one penetration enhancer. In general, a penetration enhancer is a substance that facilitates the transport of a drug across mucous membranes associated with the desired mode of administration.

Embodiments of the present disclosure provide compositions comprising one or more pharmaceutically acceptable penetration enhancers, and methods of using such compositions, which result in the improved bioavailability of oligonucleotides administered via non-parenteral modes of administration. Penetration enhancers have previously been used to improve the bioavailability of certain drugs (see, for example, Muranishi, *Crit. Rev. Ther. Drug Carrier Systems* 7:1, 1990; and Lee et al., *Crit. Rev. Ther. Drug Carrier Systems* 8:91, 1991). It has been found that the uptake and delivery of oligonucleotides can be greatly improved even when administered by non-parenteral means through the use of a number of different classes of penetration enhancers. Penetration enhancers may be classified as belonging to one of five broad categories, surfactants, fatty acids, bile salts, chelating agents, and non-chelating non-surfactants. Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, such as capric or lauric acid, or combinations or salts thereof. Other embodiments comprise methods of enhancing the oral bioavailability of an oligonucleotide, the method comprising co-administering the oligonucleotide and at least one penetration enhancer.

Compositions for administration of non-parenteral oligonucleotide compositions of can be formulated in various dosage forms such as, but not limited to, tablets, capsules, liquid syrups, soft gels, suppositories, and enemas. The term "alimentary delivery" encompasses oral, rectal, endoscopic and sublingual/buccal administration. A common requirement for these modes of administration is absorption over some portion or all of the alimentary tract and a need for efficient mucosal penetration of the administered oligonucleotide.

Other excipients that may be added to oral oligonucleotide compositions include surfactants, which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether.

Agents that enhance uptake of oligonucleotides at the cellular level may also be added to the pharmaceutical and other compositions of the present invention, such as cationic lipids (U.S. Pat. No. 5,705,188), cationic glycerol derivatives, and polycationic molecules, such as polylysine (PCT Publication No. WO 97/30731).

VI. Combination Therapy

The ERV-9 LTR oligonucleotides provided herein can be used in combination with any therapeutic agent for the treatment of diseases or disorders, such as cancer, associated with expression of ERV-9 RNA. The therapeutic agent can be delivered at the same time as the ERV-9 LTR oligonucleotide, either as part of the same composition or as separate compositions, or the ERV-9 LTR oligonucleotide and therapeutic agent can be administered at different times. When administered at different times, the therapeutic agent can either be administered before the ERV-9 LTR oligonucleotide or after the ERV-9 LTR oligonucleotide. The time between administration of the ERV-9 LTR oligonucleotide and the therapeutic agent can vary and will depend on the type of therapeutic agent selected, the cancer being treated and the subject being treated. One of skill in the art can determine an appropriate dosing schedule for each subject.

Chemotherapeutic agents include any compound useful for the treatment of hyperproliferative disorders such as cancer. There are several different groups of chemotherapeutic agents, categorized based on chemical characteristics and/or function. Some of the common types of chemotherapeutic agents, along with representative agents in these categories, are shown below in Table 1.

TABLE 1

Chemotherapeutic Agents

| Category | Function | Representative agents |
| --- | --- | --- |
| Alkylating agents | Cross-link DNA and prevent cell division | chlorambucil, cyclophosphamide, melphalan, procarbazine, thiotepa, busulfan |
| Antimetabolites | Incorporate into DNA or RNA and interfere with cell division | 5-fluorouracil, thioguanine, cytarabine, cladribine, gemcitabine, fludarabine |
| Anthracyclines | Induce free radical formation, leading to DNA breaks and inhibition of DNA synthesis | doxorubicin, idarubicin, epirubicin, mitoxantrone |
| Antitumor antibiotics | Forms oxygen free radicals causing DNA breakage | bleomycin |
| Monoclonal antibodies | Bind tumor specific antigens and target tumor cells for destruction by the immune system | alemtuzumab, bevacizumab, cetuximab, gemtuzumab, ibritumomab, panitumumab, rituximab, tositumomab, trastuzumab |
| Platinums | Cross-link DNA | cisplatin, oxaliplatin |
| Topoisomerase inhibitors | Inhibit type I or type II topoisomerases | irinotecan, topotecan, amsacrine, etoposide, etoposide phosphate, teniposide |
| Taxanes | Inhibit microtubule function | paclitaxel. docetaxel |

TABLE 1-continued

Chemotherapeutic Agents

| Category | Function | Representative agents |
|---|---|---|
| Hormone-based therapies | Inhibit activity of specific hormones or hormones receptors | finasteride, tamoxifen |

Although Table 1 lists exemplary chemotherapeutic agents that can be used in combination with the ERV-9 LTR oligonucleotides, other chemotherapeutic agents are known in the art. It is within the capabilities of one of ordinary skill in the art to select an appropriate chemotherapeutic agent for use in combination with an ERV-9 LTR oligonucleotide for the treatment of cancer.

The ERV-9 LTR oligonucleotides provided herein also can be administered in conjunction with another oligonucleotide useful in the treatment of cancer. Generally, the oligonucleotide is an antisense oligonucleotide or other antisense compound that specifically targets a gene that is up-regulated in one or more types of cancer. Selected antisense oligonucleotides that have been or are currently being tested in clinical trials are reviewed by Dean and Bennett (*Oncogene* 22:9087-9096, 2003, herein incorporated by reference).

Antisense oligonucleotides for cancer therapeutics are known in the art, and include, but are not limited, antisense oligonucleotides that target clusterin (OncoGeneX Technologies/Isis Pharmaceuticals, U.S. Pat. No. 6,383,808), HSP27 (OncoGeneX Technologies, U.S. Pat. No. 7,101,991), IGFBP (OncoGeneX Technologies, U.S. Pat. No. 7,196,067), Bcl-2 (Aventis/Genta Incorporated, U.S. Pat. No. 7,256,284), telomerase (Geron Corporation, U.S. Pat. No. 7,297,488), MDM2 (Hybridon, U.S. Pat. No. 6,946,447), protein kinase C-alpha (Isis Pharmaceuticals, U.S. Pat. No. 5,885,970), Ha-ras (Isis Pharmaceuticals, U.S. Pat. No. 6,117,848), ribonucleotide reductase (Lorus Therapeutics, U.S. Pat. No. 7,405,205), c-raf kinase (NeoPharm), TFG-B2 (Antisense Pharma), protein kinase A (Hybridon, U.S. Pat. No. 5,969,117), DNA methyltransferase (MethyGene/MGI Pharma/British Biotech), c-myc (AVI BioPharma, U.S. Pat. No. 6,869,795). Each of the above-listed U.S. patents is herein incorporated by reference.

Any known (such as those listed above) or yet to be discovered antisense oligonucleotide useful for the treatment of cancer can be used in combination with the ERV-9 LTR oligonucleotides disclosed herein.

The second therapeutic agent can be administered in a single dose or in multiple doses. When administered in multiple doses, the time period between each administration can vary and will depend in part on the subject being treated, the type of cancer being treated and the type of therapeutic agent selected.

The following examples are provided to illustrate certain particular features and/or embodiments. These examples should not be construed to limit the disclosure to the particular features or embodiments described.

EXAMPLES

Example 1

Treatment of Cancer Cells with ERV-9 Oligonucleotides

This example describes the effects of oligonucleotides specifically targeting ERV-9 LTR U3 on cancer cell proliferation. Oligonucleotides were designed to target the U3 region of the ERV-9 LTR. A sense oligonucleotide (U3S; CTCAAGGTTTGTAAACACACCAATCAG; SEQ ID NO: 1) hybridizes with the non-coding strand and an antisense oligonucleotide (U3AS; CTGATTGGTGTGTTTACAAACCTTGAG; SEQ ID NO: 2) hybridizes with the coding strand of the ERV-9 LTR U3 region. Both oligonucleotides were modified to contain phosphorothioate internucleoside linkages at each position.

Figure 2:
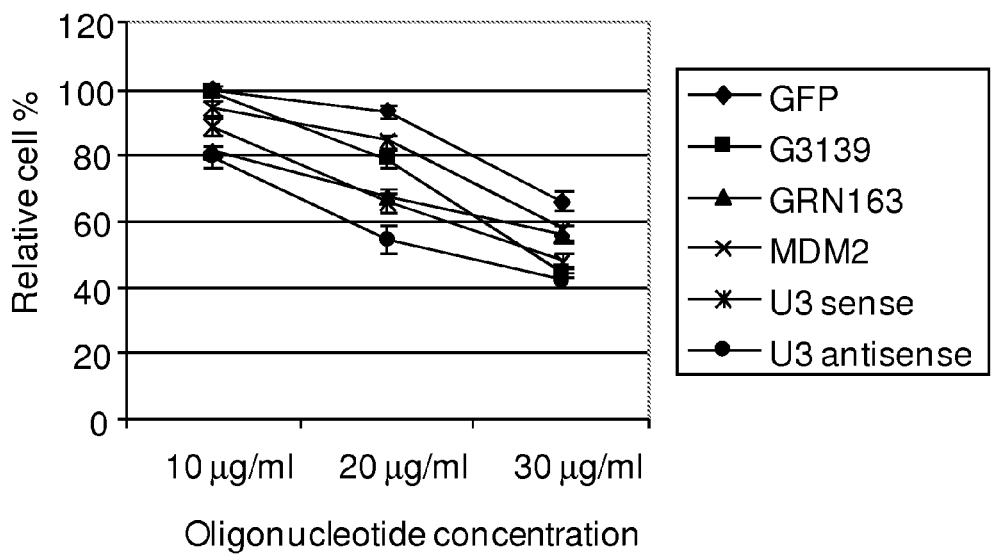
FIG. 2 is a graph showing the effect of sense and antisense ERV-9 U3 oligonucleotides (SEQ ID NOs: 1 and 2, respectively) on proliferation of MDA-231 cells (a breast cancer cell line). Cells ($4 \times 10^4$) were treated with ERV-9 U3 sense or antisense oligonucleotide formulated in LIPOFECTAMINE™ at the concentrations shown for 48 hours. ERV-9 U3 sense and antisense oligonucleotides inhibited cell proliferation better than GFP control oligonucleotide at all three oligonucleotide concentrations ($P<0.05$). In contrast, G3139 inhibited cell proliferation only at oligonucleotide concentrations of 20 µg/ml and 30 µg/ml ($P<0.05$); and GRN163 and MDM2 antisense oligonucleotides inhibited cell proliferation only at concentrations of 10 µg/ml and 20 µg/ml ($P<0.05$).
Figure 3:
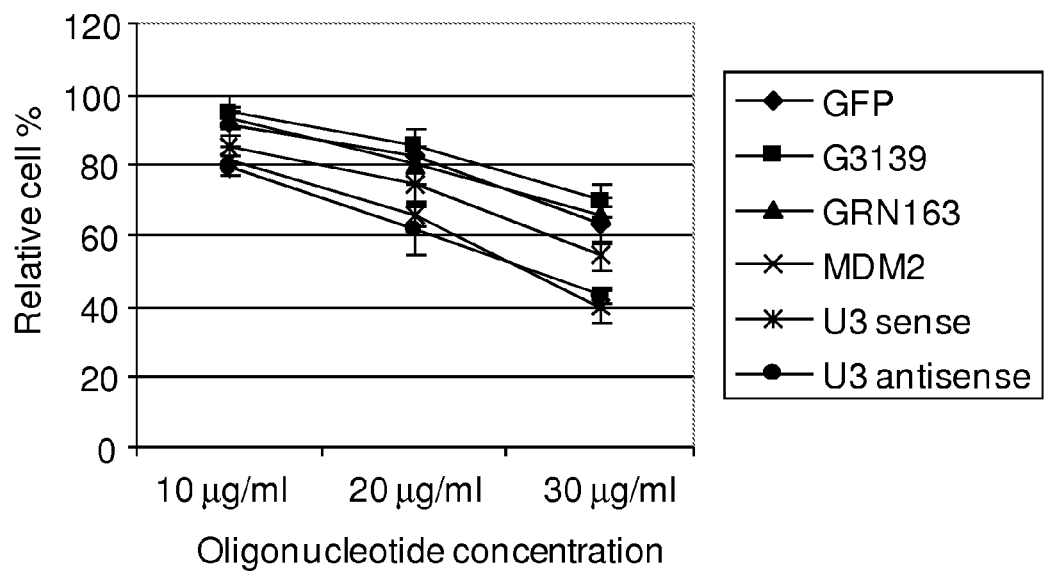
FIG. 3 is a graph showing the effect of sense and antisense ERV-9 U3 oligonucleotides (SEQ ID NOs: 1 and 2, respectively) on proliferation of K562 cells (a myelogenous leukemia cell line). Cells ($4 \times 10^4$) were treated with ERV-9 U3 sense or antisense oligonucleotide formulated in LIPOFECTAMINE™ at the concentrations shown for 48 hours. ERV-9 U3 sense and antisense oligonucleotides inhibited cell proliferation better than GFP control oligonucleotide at concentrations of 10 µg/ml and 20 µg/ml ($P<0.05$), and inhibited proliferation better than GFP control and G3139, GRN163 and MDM2 antisense oligonucleotides at a concentration of 30 µg/ml ($P<0.05$).
Figure 4:
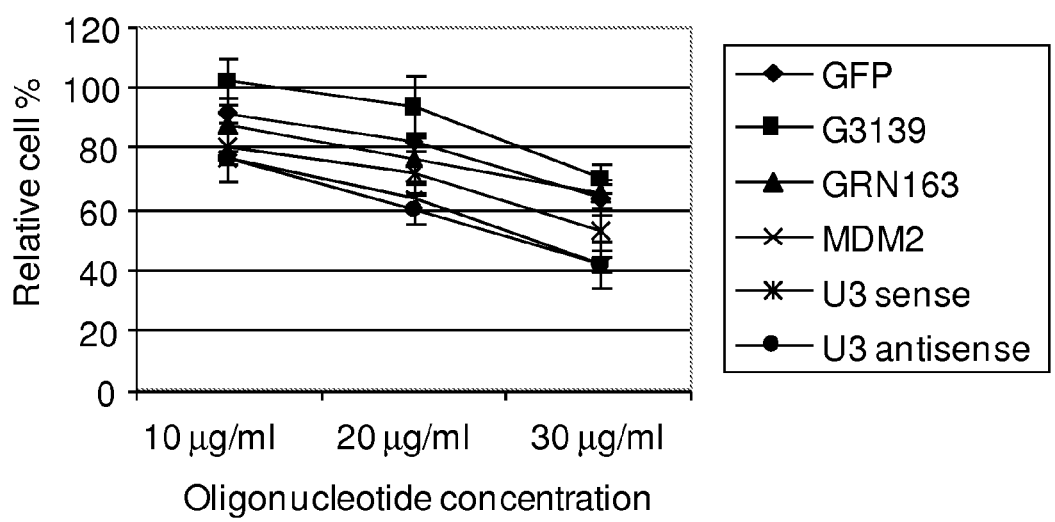
FIG. 4 is a graph showing the effect of sense and antisense ERV-9 U3 oligonucleotides (SEQ ID NOs: 1 and 2, respectively) on proliferation of LNcaP cells (a prostate cancer cell line). Cells ($4 \times 10^4$) were treated with ERV-9 U3 sense or antisense oligonucleotide formulated in LIPOFECTAMINE™ at the concentrations shown for 48 hours. ERV-9 U3 sense and antisense oligonucleotides inhibited cell proliferation better than GFP control oligonucleotide at all three oligonucleotide concentrations ($P<0.05$). In contrast, G3139 and GRN163 oligonucleotides did not significantly inhibit cell proliferation at any of the three concentration levels ($P>0.05$), and MDM2 antisense oligonucleotide inhibited cell proliferation only at a concentration of 10 µg/ml ($P<0.05$).
Figure 5:
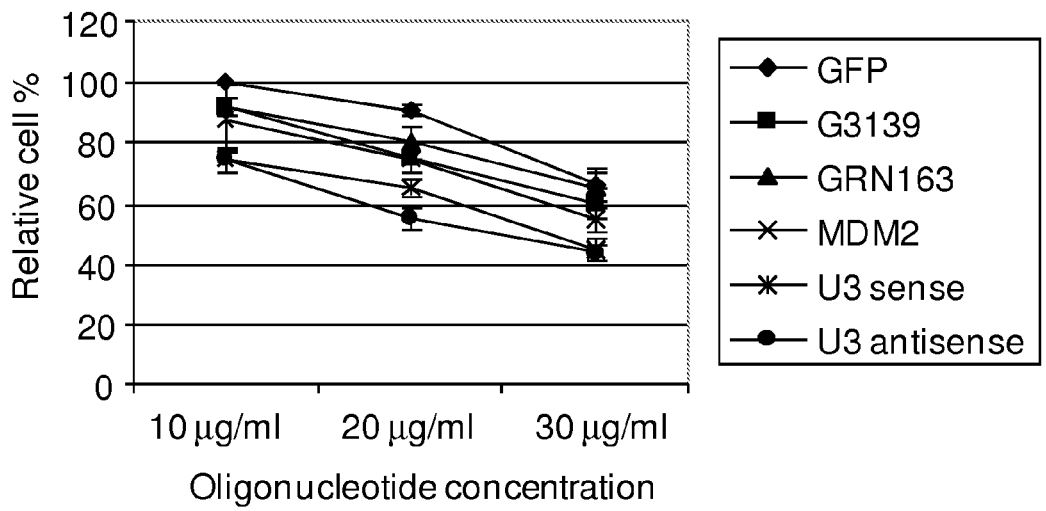
FIG. 5 is a graph showing the effect of sense and antisense ERV-9 U3 oligonucleotides (SEQ ID NOs: 1 and 2, respectively) on proliferation of HepG2 cells (a hepatocellular carcinoma cell line). Cells ($4 \times 10^4$) were treated with ERV-9 U3 sense or antisense oligonucleotide formulated in LIPOFECTAMINE™ at the concentrations shown for 48 hours. ERV-9 U3 sense and antisense oligonucleotides inhibited cell proliferation better than GFP control and G3139, GRN163 and MDM2 antisense oligonucleotides at all three concentration levels ($P<0.05$).
Figure 6:
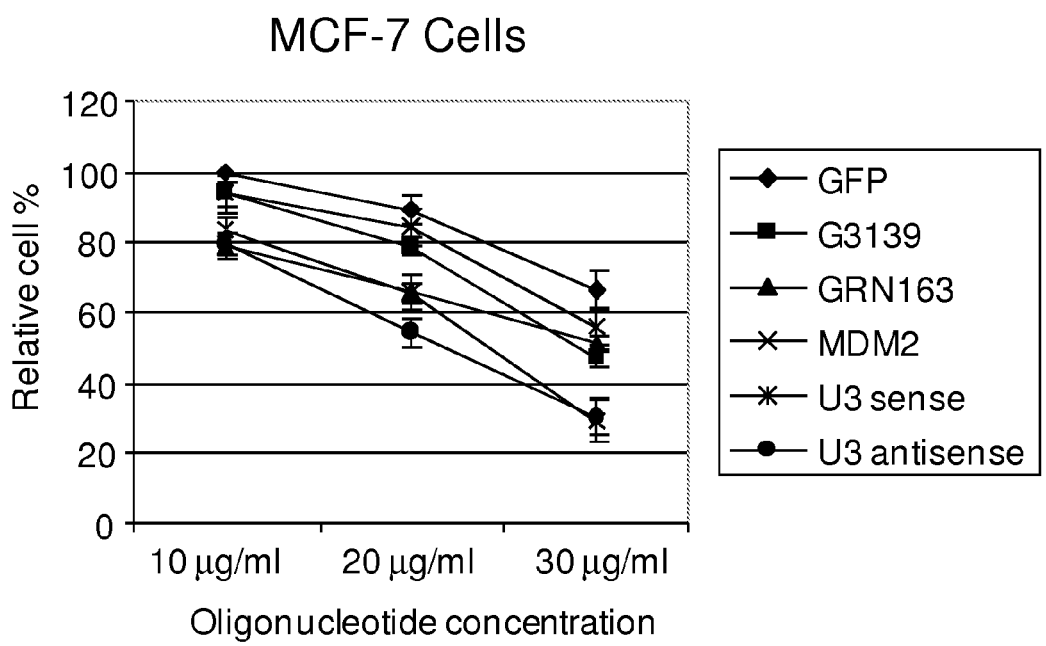
FIG. 6 is a graph showing the effect of sense and antisense ERV-9 U3 oligonucleotides (SEQ ID NOs: 1 and 2, respectively) on proliferation of MCF-7 cells (a breast cancer cell line). Cells ($4 \times 10^4$) were treated with ERV-9 U3 sense or antisense oligonucleotide formulated in LIPOFECTAMINE™ at the concentrations shown for 48 hours. ERV-9 U3 sense and antisense oligonucleotides inhibited cell proliferation better than GFP control oligonucleotide at all three concentrations ($P<0.05$), and inhibited proliferation better than G3139, GRN163 and MDM2 antisense oligonucleotides at a concentration of 30 µg/ml ($P<0.05$).

To test the effect of the sense and antisense ERV-9 U3 oligonucleotides on proliferation of cancer cells, six different cancer cell lines were selected for transfection studies: HT1080, fibrosarcoma cells (FIG. 1); MDA-231, breast cancer cells (FIG. 2); K562, myelogenous leukemia cells (FIG. 3); LNcaP, prostate cancer cells (FIG. 4); HepG2, hepatocellular carcinoma cells (FIG. 5); and MCF-7, breast cancer cells (FIG. 6). Cells ($4\times10^4$) were treated with ERV-9 U3 sense or antisense oligonucleotide formulated in LIPOFECTAMINE™ at an oligonucleotide concentration of 10, 20 or 30 µg/ml for 48 hours. Green fluorescent protein (GFP) sense oligonucleotide (CATTATCAACAAAATACTCCAATT; SEQ ID NO: 3) was used as a control to measure the non-specific cytotoxicity of phosphorothioate-based oligonucleotides. Antisense oligonucleotides specific for Bcl-2 (G3139; TCTCCCAGCGTGCGCCAT; SEQ ID NO: 4), telomerase (GRN163; TAGGGTTAGACAA; SEQ ID NO: 5), and MDM2 (TGACACCTGTTCTCACTCAC; SEQ ID NO: 6) were also evaluated. Each of these antisense oligonucleotides has been previously shown to inhibit tumor growth in animal models (U.S. Pat. Nos. 7,256,284 and 6,946,447; Ozawa et al., *Neuro-Oncology* 6:218-226, 2004). After 48 hours of oligonucleotide treatment, cell proliferation was assessed by direct cell counting. Cell proliferation levels were expressed relative to cells transfected with 10 µg/ml GFP control oligonucleotide.

As shown in FIGS. 1-6, treatment with either the ERV-9 U3 sense (SEQ ID NO: 1) or antisense (SEQ ID NO: 2) oligonucleotide resulted in a significant decrease in proliferation of each cancer cell line tested, relative to GFP control oligonucleotide. Furthermore, in most instances, the ERV-9 U3 sense and antisense oligonucleotides inhibited proliferation to a greater extent than the Bcl-2, telomerase and MDM2-specific antisense oligonucleotides.

Example 2

Treatment of Cancer Cells with ERV-9 Oligonucleotide in Combination with VP16

This example describes the effect on proliferation of cancer cell lines resulting from treatment with ERV-9 LTR U3-specific oligonucleotides in combination with a chemotherapeutic agent. VP16 (also known as etoposide, ETOPOPHOS™ or VEPESID™) is a chemotherapeutic agent that inhibits the activity of topoisomerase. VP16 is commonly used to treat a variety of cancers, including lung cancer, testicular cancer, leukemia, and lymphoma.

Figure 7:
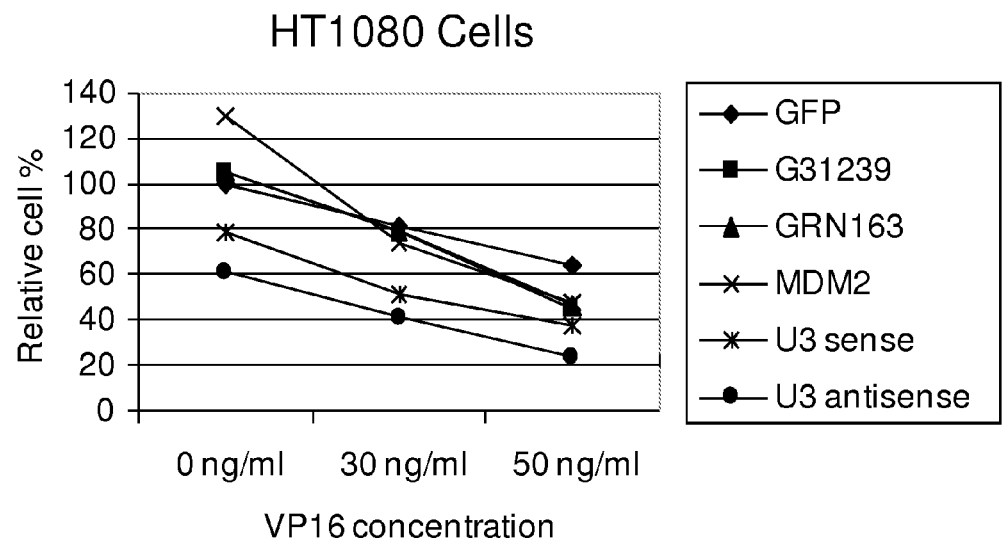
FIG. 7 is a graph showing proliferation of HT1080 cells treated with ERV-9 U3 sense or antisense oligonucleotide (SEQ ID NOs: 1 and 2, respectively), in combination with VP16 (also known as etoposide). Cells ($4 \times 10^4$) were treated with oligonucleotide (15 µg/ml) alone or in combination with the concentrations of VP16 shown for 48 hours. Cell proliferation levels were expressed relative to the percentage of GFP oligonucleotide control in the absence of VP16. ERV-9 U3 sense and antisense oligonucleotides inhibited cell proliferation better than GFP control and G3139, GRN163 and MDM2 antisense oligonucleotides at VP16 concentrations of 30 ng/ml and 50 ng/ml ($P<0.05$).
Figure 8:
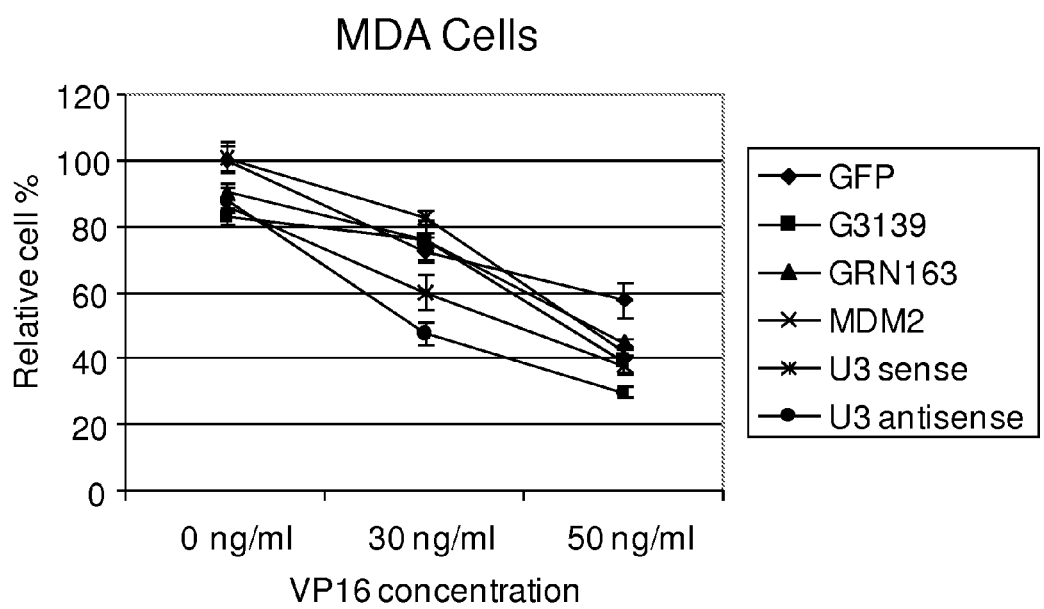
FIG. 8 is a graph showing proliferation of MDA-231 cells treated with ERV-9 U3 sense or antisense oligonucleotide (SEQ ID NOs: 1 and 2, respectively), in combination with VP16. Cells ($4 \times 10^4$) were treated with oligonucleotide (15 µg/ml) alone or in combination with the concentrations of VP16 shown for 48 hours. ERV-9 U3 sense oligonucleotide inhibited cell proliferation better than GFP oligonucleotide at VP16 concentrations of 30 ng/ml and 50 ng/ml ($P<0.05$). ERV-9 U3 antisense oligonucleotide inhibited cell proliferation better than GFP control and G3139, GRN163 and MDM2 antisense oligonucleotides at VP concentrations of 30 ng/ml and 50 ng/ml ($P<0.05$). In contrast, G3139, GRN163 and MDM3 antisense oligonucleotides inhibited cell proliferation only at a VP16 concentration of 50 ng/ml ($P<0.05$).
Figure 9:
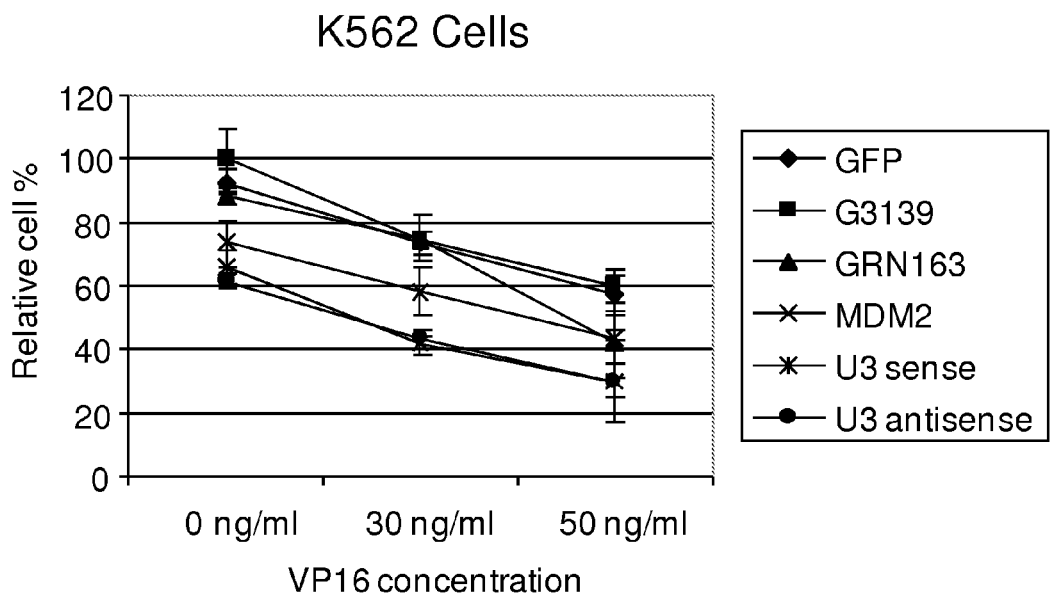
FIG. 9 is a graph showing proliferation of K562 cells treated with ERV-9 U3 sense or antisense oligonucleotide (SEQ ID NOs: 1 and 2, respectively), in combination with VP16. Cells ($4 \times 10^4$) were treated with oligonucleotide (15 µg/ml) alone or in combination with the concentrations of VP16 shown for 48 hours. ERV-9 U3 sense and antisense oligonucleotides inhibited cell proliferation better than GFP control and G3139, GRN163 and MDM2 antisense oligonucleotides at VP16 concentrations of 30 ng/ml and 50 ng/ml ($P<0.05$).
Figure 10:
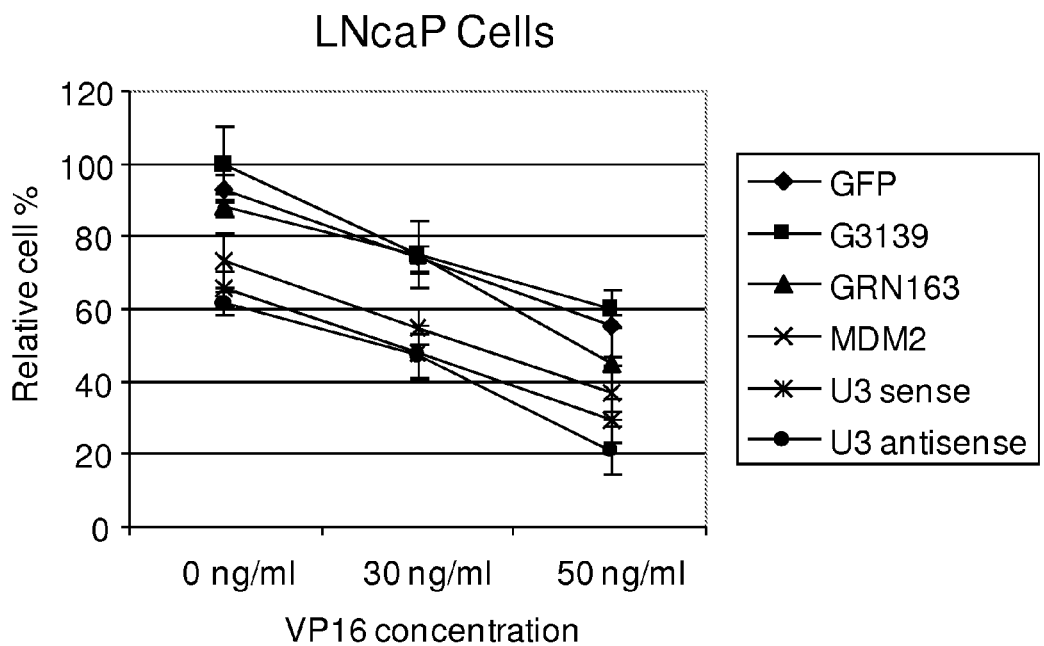
FIG. 10 is a graph showing proliferation of LNcaP cells treated with ERV-9 U3 sense or antisense oligonucleotide (SEQ ID NOs: 1 and 2, respectively), in combination with VP16. Cells ($4 \times 10^4$) were treated with oligonucleotide (15 µg/ml) alone or in combination with the concentrations of VP16 shown for 48 hours. ERV-9 U3 sense and antisense oligonucleotides inhibited cell proliferation better than GFP oligonucleotide at VP16 concentrations of 30 ng/ml and 50 ng/ml ($P<0.05$). Relative to GFP control, G3139 and GRN163 antisense oligonucleotides did not inhibit cell proliferation at any VP16 concentration tested ($P>0.05$). MDM2 antisense oligonucleotide inhibited cell proliferation better than GFP control only at a VP16 concentration of 30 ng/ml ($P<0.05$).
Figure 11:
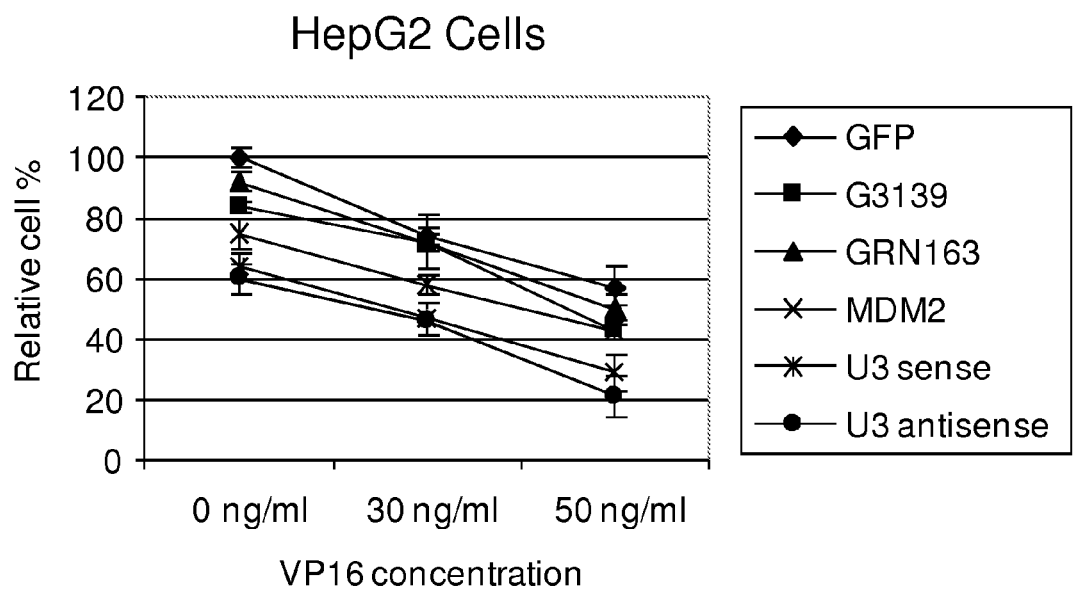
FIG. 11 is a graph showing proliferation of HepG2 cells treated with ERV-9 U3 sense or antisense oligonucleotide (SEQ ID NOs: 1 and 2, respectively), in combination with VP16. Cells ($4 \times 10^4$) were treated with oligonucleotide (15 µg/ml) alone or in combination with the concentrations of VP16 shown for 48 hours. ERV-9 U3 sense and antisense oligonucleotides inhibited cell proliferation better than GFP control and G3139, GRN163 and MDM2 antisense oligonucleotides at VP16 concentrations of 30 ng/ml and 50 ng/ml (P<0.05).
Figure 12:
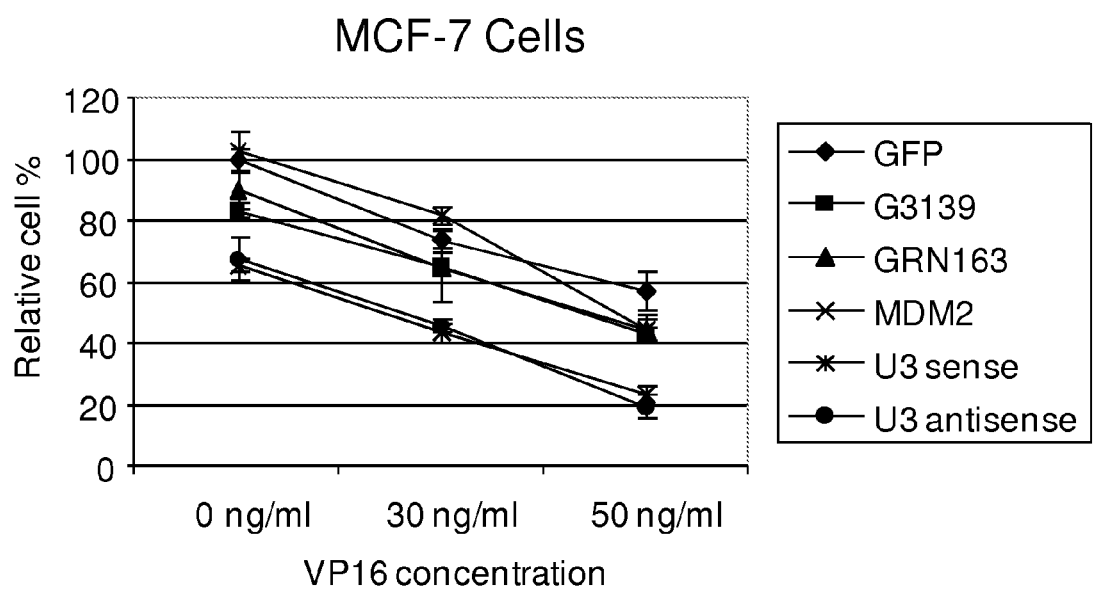
FIG. 12 is a graph showing proliferation of MCF-7 cells treated with ERV-9 U3 sense or antisense oligonucleotide (SEQ ID NOs: 1 and 2, respectively), in combination with VP16. Cells ($4 \times 10^4$) were treated with oligonucleotide (15 μg/ml) alone or in combination with the concentrations of VP16 shown for 48 hours. ERV-9 U3 sense and antisense oligonucleotides inhibited cell proliferation better than GFP control and G3139, GRN163 and MDM2 antisense oligonucleotides at VP16 concentrations of 30 ng/ml and 50 ng/ml (P<0.05).

To test the effect of treating cancer cells with the combination of ERV-9 U3 oligonucleotide and VP16, six different cancer cell lines were analyzed: HT1080, (FIG. 7); MDA-231 (FIG. 8); K562 (FIG. 9); LNcaP (FIG. 10); HepG2 (FIG. 11); and MCF-7 (FIG. 12). Cells ($4\times10^4$) were treated with 15 µg/ml ERV-9 U3 sense (SEQ ID NO: 1) or antisense (SEQ ID NO: 2) oligonucleotide alone or in combination with VP16 at a concentration of 30 ng/ml or 50 ng/ml. After 48 hours, cell proliferation was assessed by direct cell counting. Cell proliferation levels were expressed relative to GFP oligonucleotide control in the absence of VP16.

As shown in FIGS. 7-12, treatment with either the ERV-9 U3 sense or antisense oligonucleotide resulted in a significant decrease in proliferation of each cancer cell line tested, relative to GFP control oligonucleotide. Furthermore, combination treatment with VP16 resulted in a dose-dependent reduction in cell proliferation. In most instances, the ERV-9 U3 sense and antisense oligonucleotides inhibited proliferation to a greater extent than the Bcl-2, telomerase and MDM2-specific antisense oligonucleotides, either alone or in combination with VP16.

compared with U3S and U3AS. The sequence and ERV-9 LTR target site of each oligonucleotide (Oligo) is shown in Table 2. Oligonucleotides are designated U3 or U5 depending on which region of the LTR they bind and "S" for sense or "AS" for antisense.

TABLE 2

ERV-9 LTR Oligonucleotides

| Oligo | Sequence | SEQ ID NO: | Target Site (GenBank Accession No.) |
|---|---|---|---|
| U3S | CTCAAGGTTTGTAAACACACCAATCAG | 1 | nt 3329-3355 (AF064190) |
| U3AS | CTGATTGGTGTGTTTACAAACCTTGAG | 2 | nt 3329-3355 (AF064190) |
| U3S4 | CCGAGCCTCGCCGACGAGCGCCGC | 7 | nt 3096-3119 (AF064190) |
| U3AS4 | GCGGCGCTCGTCGGCGAGGCACGG | 8 | nt 3096-3119 (AF064190) |
| U3S5 | GGCTGGCCAAGGCCAGAGCCGGCTCC | 9 | nt 2792-2817 (AF064190) |
| U3AS5 | CCGACCGGTTCCGGTCTCGGCCGAGG | 10 | nt 2792-2817 (AF064190) |
| U5S | GAACACATCCAAACATCAGAAC | 11 | nt 819-840 (AF064191) |
| U5AS | GTTCTGATGTTTGGATGTGTTC | 12 | nt 819-840 (AF064191) |

Example 3

Effect of ERV-9 Oligonucleotides on Proliferation of Normal Human Cells

Figure 13:
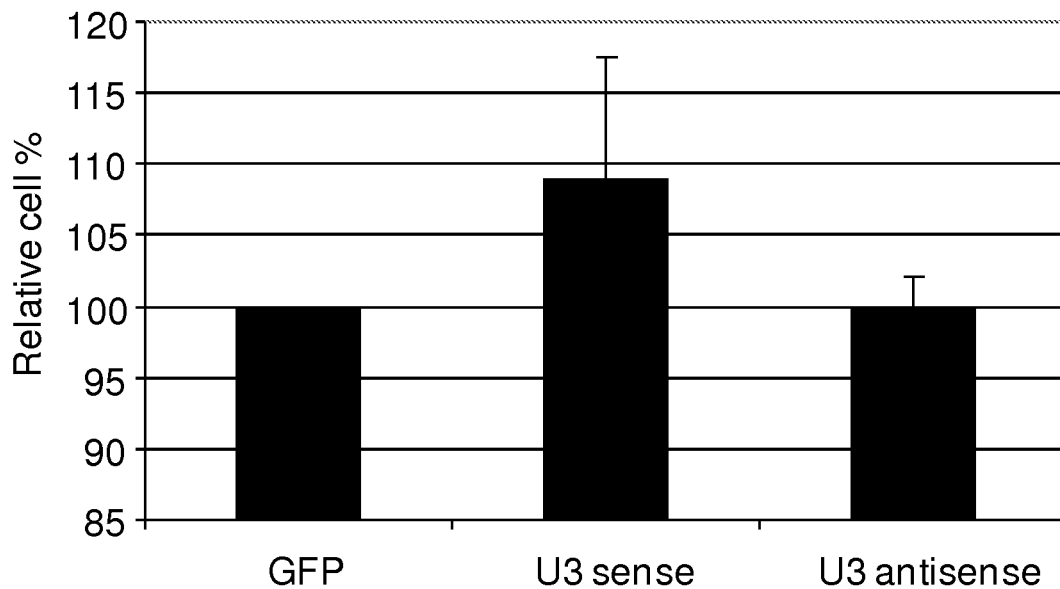
FIG. 13 is a graph showing the effect of ERV-9 U3 sense and antisense oligonucleotides (SEQ ID NOs: 1 and 2, respectively) on human primary keratinocytes. Cells ($4 \times 10^4$) were transfected with ERV-9 U3 sense or antisense oligonucleotide formulated in LIPOFECTAMINE™ at a concentration of 20 μg/ml for 48 hours. GFP oligonucleotide was used as non-specific phosphorothioate oligonucleotide control. ERV-9 U3 sense and antisense oligonucleotides did not inhibit cell proliferation relative to control GFP oligonucleotide (P>0.05).
Figure 14:
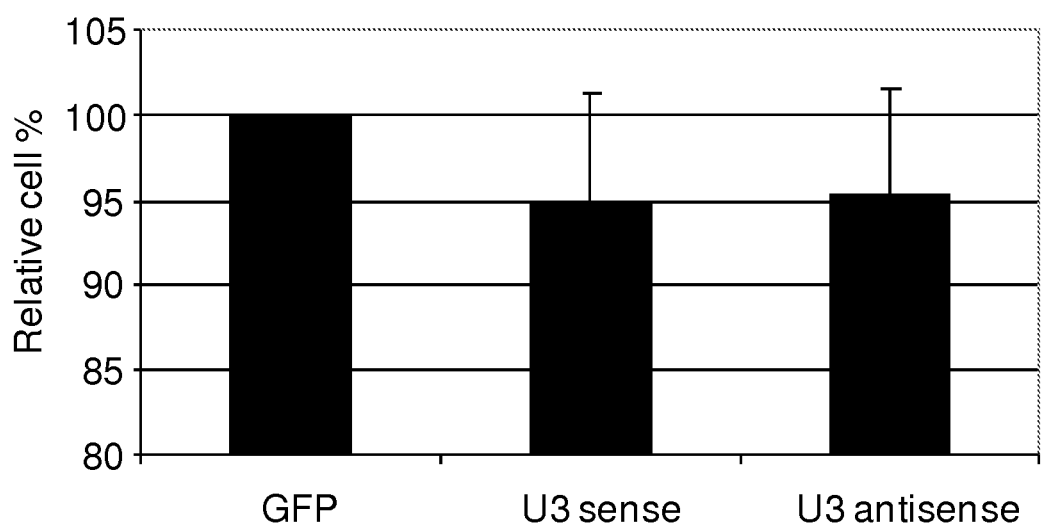
FIG. 14 is a graph showing the effect of ERV-9 U3 sense and antisense oligonucleotides (SEQ ID NOs: 1 and 2, respectively) on human primary lymphocytes. Cells ($4 \times 10^4$) were transfected with ERV-9 U3 sense or antisense oligonucleotide formulated in LIPOFECTAMINE™ at a concentration of 20 μg/ml for 48 hours. ERV-9 U3 sense and antisense oligonucleotides did not inhibit cell proliferation relative to control GFP oligonucleotide (P>0.05).
Figure 15:
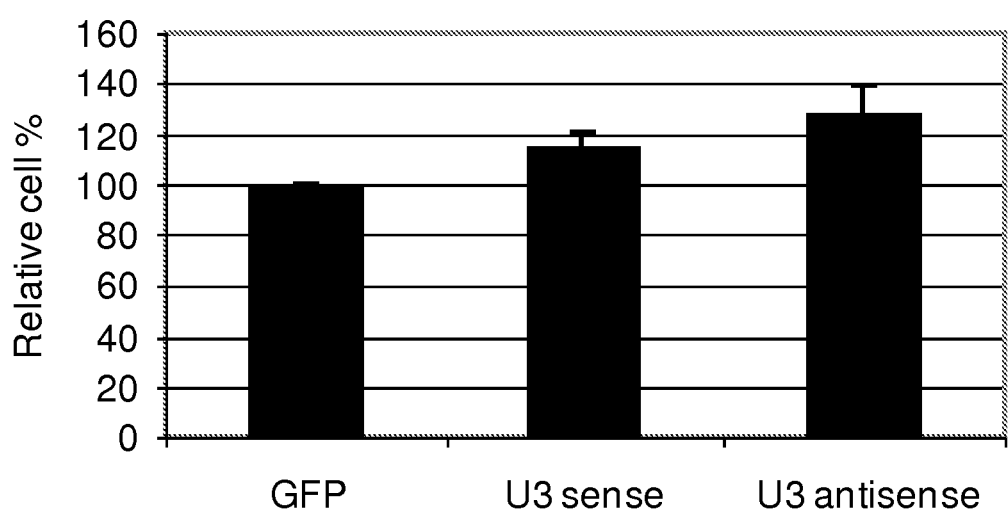
FIG. 15 is a graph showing the effect of ERV-9 U3 sense and antisense oligonucleotides (SEQ ID NOs: 1 and 2, respectively) on human primary monocytes. Cells ($4 \times 10^4$) were transfected with ERV-9 U3 sense or antisense oligonucleotide formulated in LIPOFECTAMINE™ at a concentration of 20 μg/ml for 48 hours. ERV-9 U3 sense and antisense oligonucleotides did not inhibit cell proliferation relative to control GFP oligonucleotide (P>0.05).

This example describes the finding that treatment with ERV-9 U3 sense or antisense oligonucleotide does not significantly alter proliferation of normal human primary cells. To determine whether the inhibitory effect of ERV-9 U3 oligonucleotides is specific to cancer cells, human primary keratinocytes (FIG. 13), lymphocytes (FIG. 14), or monocytes (FIG. 15) were treated with ERV-9 U3 sense or antisense oligonucleotide and cell proliferation was evaluated. Cells ($4 \times 10^4$) were transfected with ERV-9 U3 sense or antisense oligonucleotide (SEQ ID NOs: 1 and 2, respectively) formulated in LIPOFECTAMINE™ at a concentration of 20 μg/ml. GFP oligonucleotide was used as non-specific phosphorothioate oligonucleotide control. After 48 hours, cell proliferation was assessed by direct cell counting. Cell proliferation levels were expressed relative to GFP control. As shown in FIGS. 13-15, ERV-9 U3 sense and antisense oligonucleotides did not significantly alter cell proliferation of human primary cells, relative to control GFP oligonucleotide ($P>0.05$).

Example 4

ERV-9 U3 and U5 Oligonucleotides that Inhibit Cancer Cell Proliferation

Figure 16:
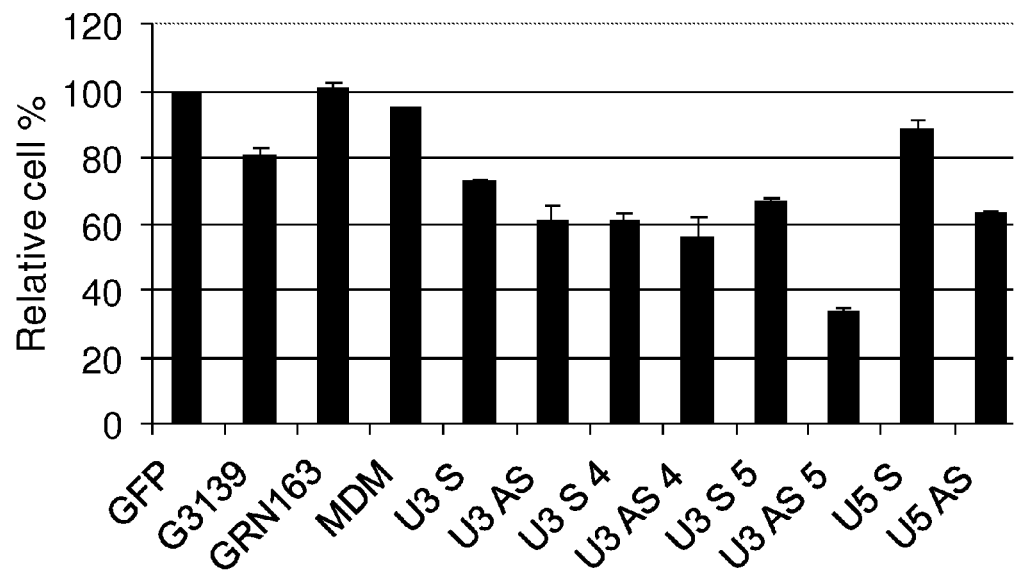
FIG. 16 is a graph showing the effect of sense and antisense ERV-9 U3 (SEQ ID NOs: 1, 2, 7, 8, 9, and 10) and U5 (SEQ ID NOs: 11 and 12) oligonucleotides on proliferation of HT1080 cells. Cells ($4 \times 10^4$) were treated with oligonucleotide formulated in LIPOFECTAMINE™ at a concentration of 20 μg/ml for 72 hours. GFP sense oligonucleotide was used as a control to measure the non-specific cytotoxicity of phosphorothioate-based oligonucleotides. Antisense oligonucleotides G3139, GRN163, and MDM2 were also evaluated. Cell proliferation levels were expressed relative to cells transfected with GFP oligonucleotide. All U3 and U5 sense and antisense oligonucleotides inhibited cell proliferation to a greater extent that GFP control. In addition, with the exception of the U5 sense oligonucleotide, all U3 and U5 oligonucleotides inhibited cell proliferation better than the G3139, GRN163 and MDM2 antisense oligonucleotides.
Figure 17:
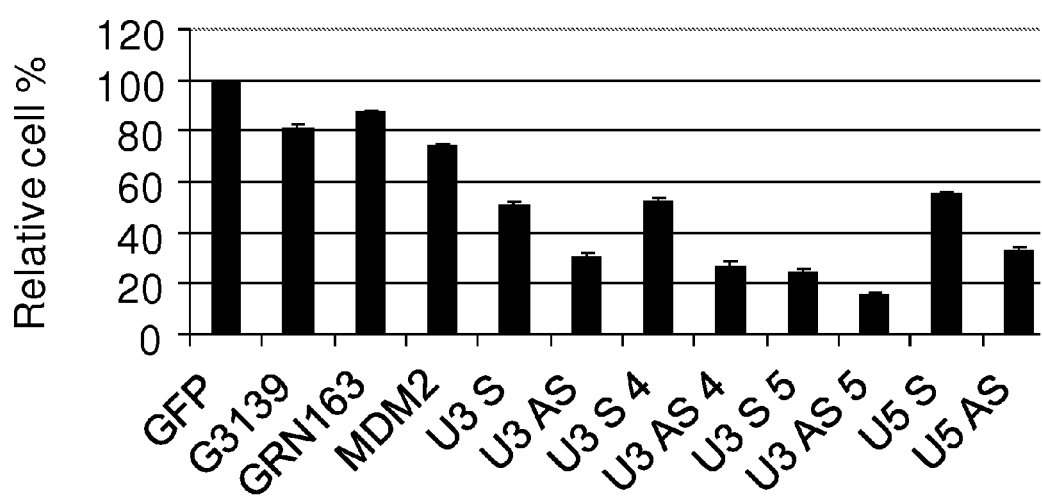
FIG. 17 is a graph showing the effect of sense and antisense ERV-9 U3 and (SEQ ID NOs: 1, 2, 7, 8, 9, and 10) and U5 (SEQ ID NOs: 11 and 12) oligonucleotides on proliferation of MDA-231 cells. Cells ($4 \times 10^4$) were treated with oligonucleotide formulated in LIPOFECTAMINE™ at a concentration of 20 μg/ml for 72 hours. GFP sense oligonucleotide and G3139, GRN163 and MDM2 antisense oligonucleotides were included as controls. Cell proliferation levels were expressed relative to cells transfected with GFP oligonucleotide. All U3 and U5 sense and antisense oligonucleotides inhibited cell proliferation better than GFP control and the G3139, GRN163 and MDM2 antisense oligonucleotides.

This example describes the identification of additional ERV-9 LTR oligonucleotides that inhibit proliferation of cancer cells lines. Four additional U3-specific and two U5-specific oligonucleotides were tested in two cancer cell lines and HT1080 or MDA-231 cells ($4 \times 10^4$ cells) were treated with ERV-9 LTR (U3 or U5) sense or antisense oligonucleotides formulated in LIPOFECTAMINE™ at a concentration of 20 μg/ml for 72 hours. GFP sense oligonucleotide was used as a control to measure the non-specific cytotoxicity of phosphorothioates-based oligonucleotides. Relative cell proliferation levels were expressed as percentage of GFP oligonucleotide transfected control. The results are shown in FIG. 16 (HT1080 cells) and FIG. 17 (MDA-231 cells).

In HT1080 cells, G3139, MDM2 and U5S oligonucleotides inhibited cell proliferation better than the GFP oligonucleotide control ($P<0.002$). U3S, U3AS, U3S4, U3AS4, U3S5, U3AS5 and U5AS oligonucleotides inhibited cell proliferation better than G3139, GRN163 and MDM2 oligonucleotides ($P<0.003$).

In MDA-231 cells, G3139, GRN163 and MDM2 antisense oligonucleotides inhibited cell proliferation better than the GFP control oligonucleotide ($P<0.001$). All U3 and U5 oligonucleotides inhibited cell proliferation better than G3139, GRN163 and MDM2 ($P<0.001$).

These results demonstrate that each of the U3- and U5-specific oligonucleotides is capable of significantly inhibiting proliferation of cancer cells.

Example 5

Treatment of Tumors with ERV-9 Oligonucleotides In Vivo

This example describes the effect of ERV-9 sense and antisense RNAs on the growth of human tumors (xenografts) in mice.

CB-17 prkdc(SCID) male, 4- to 6-week-old SCID mice were purchased from the Jackson Laboratory. Cultured cells (MDA-231 or HT1080 cells) were washed with and resuspended in serum-free media. The suspension ($2 \times 10^6$ cells in 0.2 ml per mouse) was then injected into the chest area of the mice. The mice were monitored by measuring tumor growth and body weight and by general clinical observation. When tumor size reached approximately $4 \times 4$ mm, tumor-bearing mice were randomly divided into multiple treatment and control groups (five mice per group). All oligonucleotides, dissolved in PBS, were injected into the surrounding area of the tumor at doses of 50 μg per mouse (approximately 2.5 mg/kg), one time per day, 5 days/week until the tumor size of the control injected tumors reached about 20×20 mm (2×2 cm). The tumors were dissected from mice and weighed with the investigator blinded as to the treatment group. In combination therapy, 50 μg of the oligonucleotide (approximately 2.5 mg/kg) and 50 ng of VP16 (approximately 2.5 μg/kg), both dissolved in PBS, were injected together (one time per day, 5 days/week) into the surrounding area of the tumor to all groups.

Figure 18A:
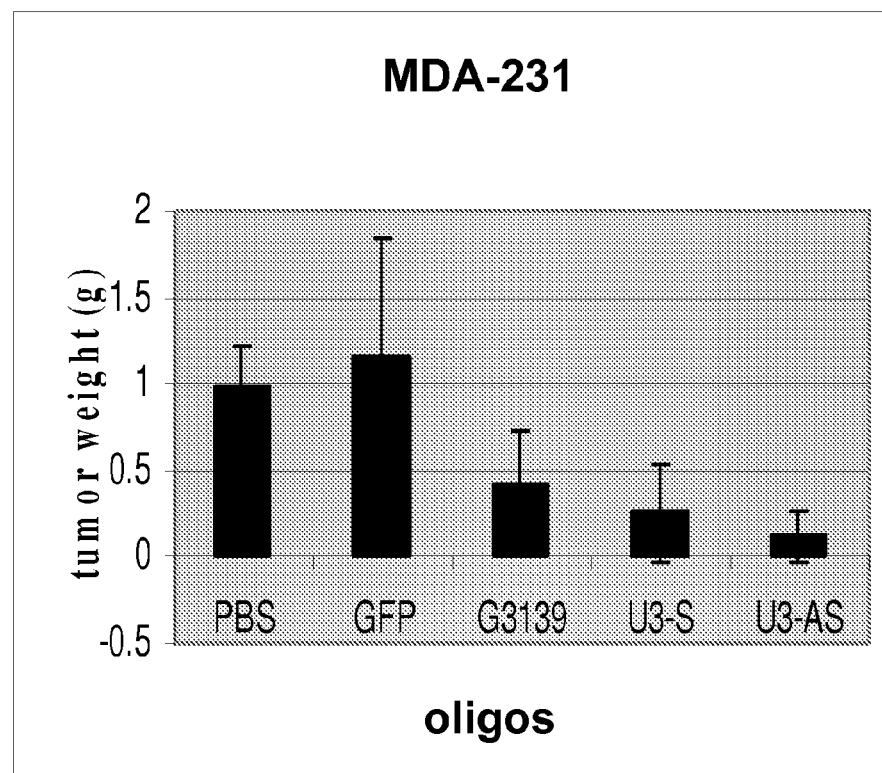
FIG. 18A is a pair of graphs showing the effect of sense and antisense ERV-9 U3 oligonucleotides (SEQ ID NOs: 1 and 2, respectively) on growth of MDA-231 (top) and HT1080 (bottom) tumor xenografts in SCID mice. Mice were injected with 50 μg of the indicated oligonucleotides once per day for 14 days (MDA-231) or 7 days (HT1080). U3 sense and antisense oligonucleotides inhibited tumor growth better than GFP oligonucleotide or G3139 antisense oligonucleotides.
Figure 18A:
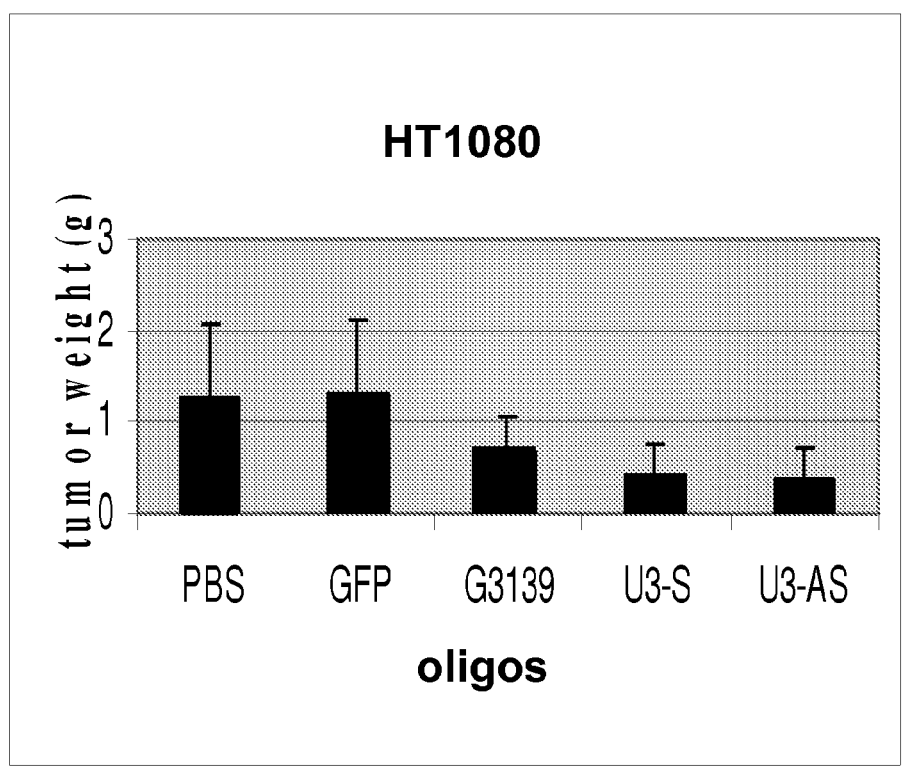
Figure 18B:
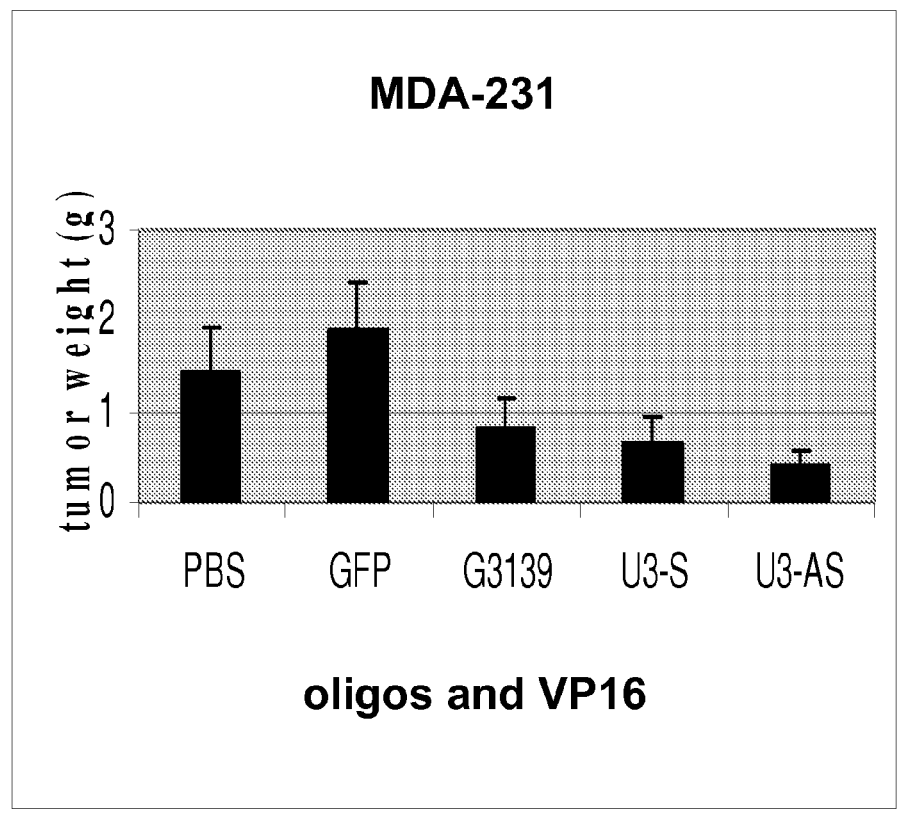
FIG. 18B is a pair of graphs showing the effect of sense and antisense ERV-9 U3 oligonucleotides (SEQ ID NOs: 1 and 2, respectively) on growth of MDA-231 (top) and HT1080 (bottom) tumor xenografts in SCID mice in combination with VP16. Mice were injected with 50 μg of the indicated oligonucleotides and 50 ng of VP16 once per day for 24 days (MDA-231) or 14 days (HT1080). U3 sense and antisense oligonucleotides inhibited tumor growth when co-administered with VP16 better than GFP oligonucleotide or G3139 antisense oligonucleotide.
Figure 18B:
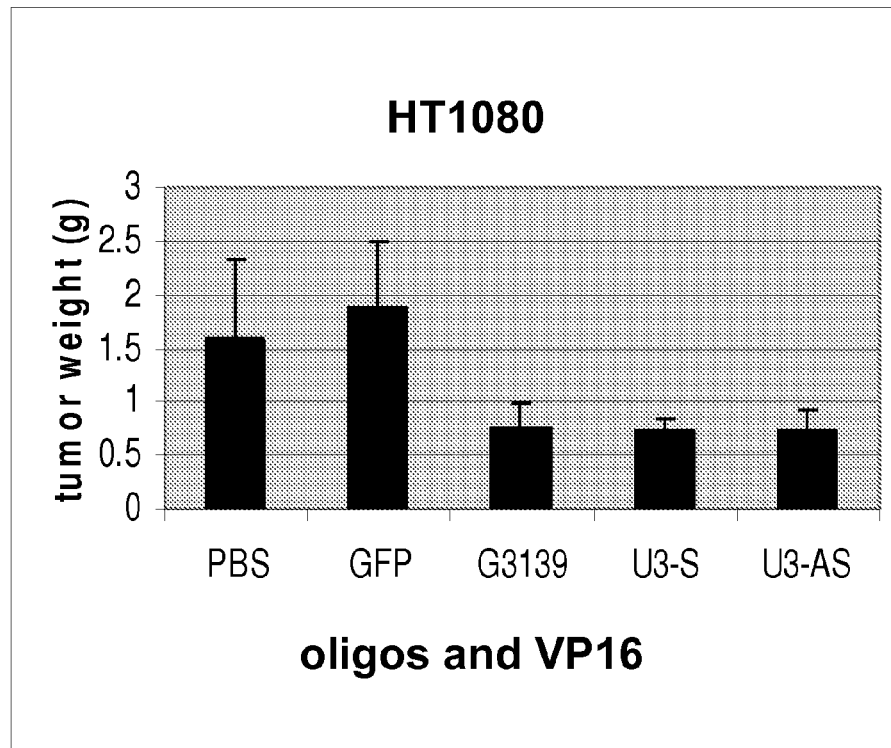

Treatment with either the U3 sense (SEQ ID NO: 1) or U3 antisense (SEQ ID NO: 2) oligonucleotide was better than treatment with PBS and GFP controls with regard to reduction of tumor size for both MDA-231 and HT1080 tumors (P<0.05) (FIG. 18A). As compared to treatment with G3139 (Bcl-2 antisense, positive control), tumor-bearing mice treated with ERV-9 U3 sense and antisense oligonucleotides had reduced tumor burden for both MDA-231 and HT1080 tumors, although this did not reach statistical significance. For combination treatment with VP-16, U3 sense and antisense as well as G3139 oligonucleotides were better than PBS and GFP controls for both MDA-231 and HT1080 tumors (P<0.05) (FIG. 18B).

Example 6

Detection of ERV-9 Sense and Antisense RNAs in Normal and Tumor Cell Lines

This example describes the finding that both sense and antisense ERV-9 LTR RNAs are expressed in tumor cells. Semi-quantitative directional RT-PCR assays were used to detect sense and antisense ERV-9 RNA in tumor and normal cells. Total RNA was isolated from primary fibroblasts, HT1080 (fibrosarcoma cell line), peripheral blood lymphocytes (PBL), K562 (myelogenous leukemia cell line), MDA-231 (breast cancer cell line), primary keratinocytes, primary testis tissue, placental tissue, primary breast cancer, and normal breast tissue. Total RNA was treated with DNase I to eliminate DNA contamination. The forward primer (CCTGAGTTTGCTGGGGATGCGAA; SEQ ID NO: 21; located nine base pairs upstream of the 5' U3 repeat region) was used for cDNA synthesis to detect the antisense RNA strand while the reverse primer (ACCCTGAGCTAGACACAGGGTGC; SEQ ID NO: 22; located at repeat number three in the U3 repeat region) was used for cDNA synthesis to detect the sense RNA strand. One μg total RNA was used for cDNA synthesis.

Figure 19:
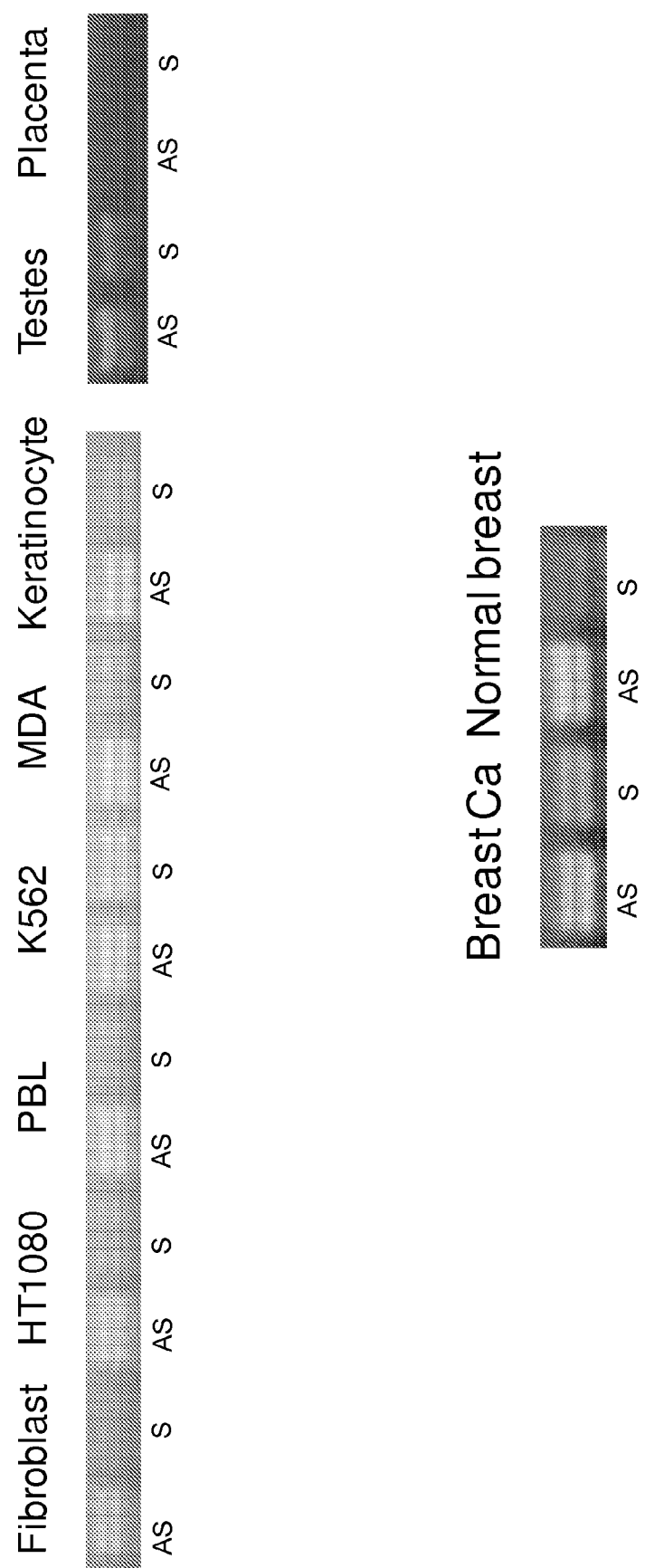
FIG. 19 is a series of images of gels showing the results of semi-quantitative directional RT-PCR assays for detection of sense (S) and antisense (AS) RNA expression from the ERV-9 LTR U3 repeat region in human primary human fibroblasts, HT1080 cells, peripheral blood lymphocytes (PBL), K562 cells, MDA-231 cells (MDA), primary keratinocytes, primary testes tissue, placental tissue, primary breast cancer tissue (Breast Ca), and normal breast tissue.

The results are shown in FIG. 19. The forward primer detected two antisense RNAs (140 bp and 200 bp), and the reverse primer detected two sense RNAs (140 bp and 200 bp). Placenta was the only tissue that had no expression of either antisense or sense RNAs of ERV-9 LTR RNA. Antisense RNAs were always relatively more abundant than sense RNAs in each cell line tested. When RNA from normal breast tissue and a breast tumor sample from the same individual was analyzed, the breast tumor sample had strong expression of both antisense and sense RNA, while the normal breast tissue had strong expression of antisense RNA, but only weak expression of sense RNA. Similarly, when primary fibroblasts and a fibrosarcoma cell line (HT1080) were compared, both strongly expressed antisense RNA, but sense RNA expression was higher in the HT1080 cells than the primary fibroblast.

Further cloning and sequencing of the antisense and sense RNA products indicated that all four RNA products (AS 140 bp, 200 bp and S 140 bp and 200 bp) arose from ERV-9 LTR U3 sequences from different chromosomal locations, and that complementary antisense and sense RNAs had the potential to form RNA duplexes.

These directional RT-PCR data indicate that both sense and antisense RNA of the ERV-9 LTR U3 region are expressed in all cells tested thus far, with sense RNA expressed at a lower level than antisense RNA in all cells tested. However, tumor cells appear to have increased sense RNA levels compared to normal cells from the same tissue.

The finding that both sense and antisense ERV-9 RNA are expressed in tumor cell lines provides support for the use of both ERV-9 sense and antisense oligonucleotides as taught herein. The present disclosure describes the use of ERV-9 U3 sense oligonucleotides to diminish or eliminate the U3 antisense RNA transcript and ERV-9 U3 antisense oligonucleotides to diminish or eliminate the U3 sense RNA transcript in human cells. It was determined that diminution or elimination of these respective strands impacted tumor cell proliferation, but that the antisense oligonucleotide more potently inhibited tumor cell proliferation (relative to the sense oligonucleotide). Furthermore, neither U3 sense nor antisense oligonucleotides had an effect on the proliferation of human primary cells (Example 3).

Example 7

Effect of ERV-9 siRNA on Proliferation of Tumor Cells

This example describes the finding that ERV-9 U3 siRNA inhibits the growth of breast cancer cell lines. SiRNAs have emerged as alternative to classic DNA oligonucleotides (ODNs) because they are more efficient and more resistant to degradation (Bertrand et al., *Biochem. Biophys. Res. Commun.* 296:1000-1004, 2002). An siRNA duplex of the ERV9 LTR U3 region was tested for potential to inhibit cell proliferation. The siRNA oligonucleotides had the sequences CUCAAGGUUUGUAAACACACCAAUCAG (SEQ ID NO: 13) and CUGAUUGGUGUGUUUACAAACCUUGAG (SEQ ID NO: 14).

$4 \times 10^4$ cells were treated with siRNAs formulated in LIPOFECTAMINE™ at 100 nM for 72 hours. Three SiRNAs (Invitrogen, RRM2HSS: GCCUGAUGUUCAAACACCUGGUACA; SEQ ID NO: 15; CCUGUGAAGCUCAUUGGGAUGAAUU; SEQ ID NO: 16; and ACCAUGAUAUCUGGCAGAUGUAUAA; SEQ ID NO: 17) against ribonucleotide reductase subunit M2 (RRM2), reported to have inhibitory effects on growth of cancer cell lines (Reid et al., *J. RNAi Gene Silenc.* 5:321-330, 2009), were used as a positive control. For RRM2, a combination of the 3 siRNAs was used at final concentration of 100 nM. Relative cell proliferation levels were expressed as percentage of non-treated control. Student's t-test was used for statistics.

Figure 20:
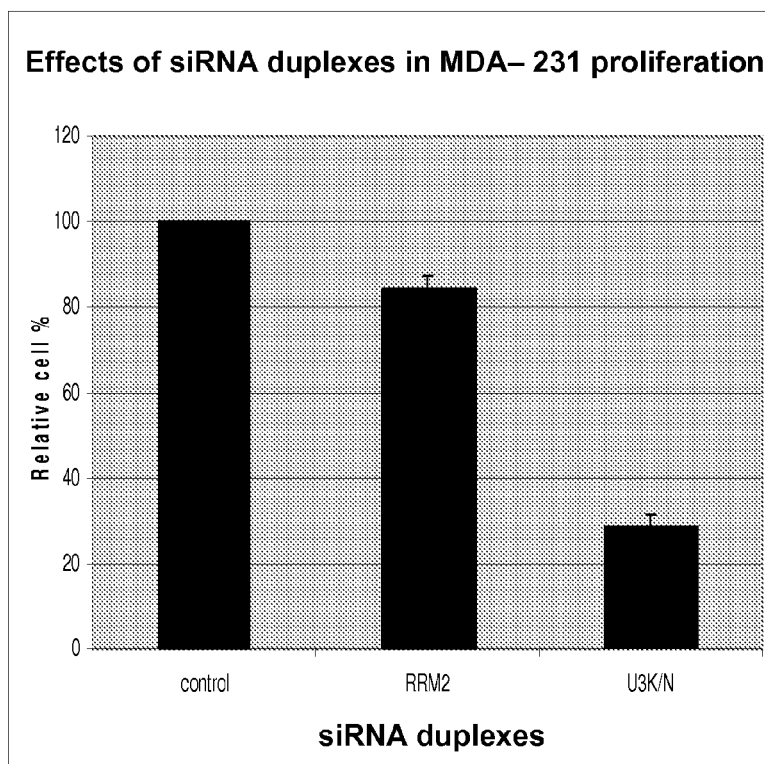
FIG. 20 is a pair of graphs showing the effect of ERV-9 LTR U3 region siRNA (SEQ ID NOs: 13 and 14), alone or in combination with VP16, on proliferation of MDA-231 (top) and MCF-7 (bottom) cells. $4 \times 10^4$ cells were treated with siRNAs formulated in LIPOFECTAMINE™ at 100 nM for 72 hours. RRM2 is a combination of three siRNAs (SEQ ID NOs: 15, 16, and 17) against ribonucleotide reductase subunit M2. Relative cell proliferation levels were expressed as percentage of non-treated control.
Figure 20:
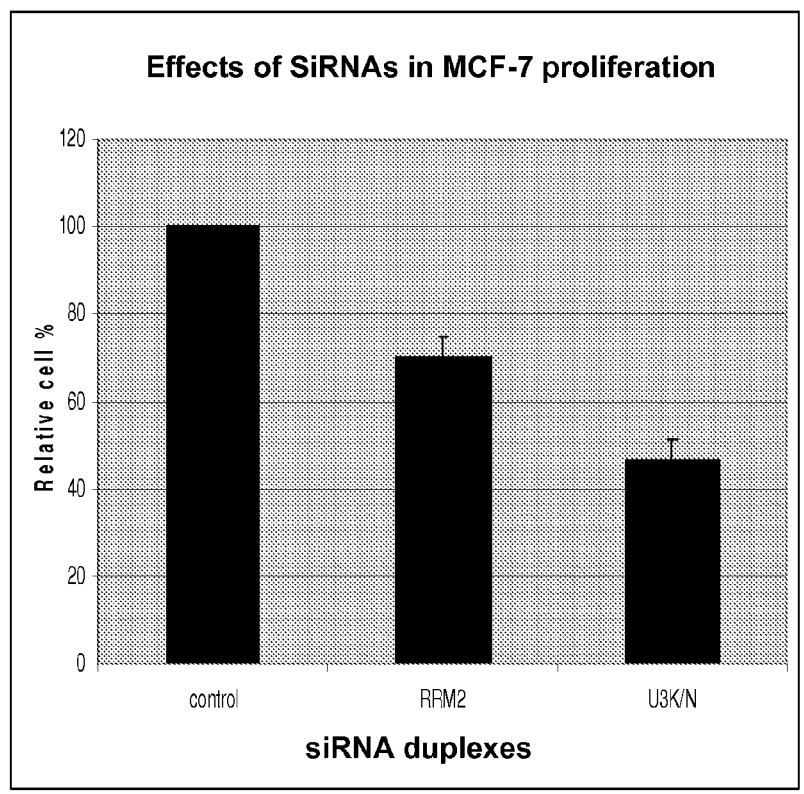

The results are shown in FIG. 20. In MDA-231 cells, RRM2 siRNAs inhibited cell proliferation better than control (P<0.003), and ERV-9 LTR U3 siRNA (SEQ ID NOs: 14 and 15) inhibited cell proliferation better than RRM2 siRNAs (P<0.001). In MCF-7 cells, RRM2 siRNAs inhibited cell proliferation better than control (P<0.001), and ERV-9 LTR U3 siRNA (SEQ ID NO: 14 and 15) inhibited cell proliferation better than RRM2 siRNAs (P<0.001). The concentration of ERV-9 U3 siRNA used in these experiments was about 10-20 times lower than the concentration of U3 sense (SEQ ID NO: 1) and antisense (SEQ ID NO: 2) DNA oligonucleotides used in previous experiments (Examples 1-4). Thus ERV9 LTR U3 siRNA has the potential for increasing the sensitivity of the treatment.

Example 8

Use of ERV-9 U3 Oligonucleotide(s) for the Treatment of a Subject Diagnosed with Cancer This example describes a representative method for treatment of a patient diagnosed with prostate cancer with an ERV-9 U3 oligonucleotide. However, one skilled in the art will appreciate that methods that deviate from these specific methods can also be used to successfully treat a subject with cancer, including cancers other than prostate cancer.

A prostate cancer patient that has recently undergone prostatectomy is selected for treatment. An ERV-9 U3 antisense and/or sense oligonucleotide (such as SEQ ID NO: 1 or SEQ ID NO: 2) is formulated at a concentration of 10 mg/ml in an isotonic, phosphate-buffered saline solution (pH 7.4) for intravenous administration. The patient is administered three doses of ERV-9 U3 oligonucleotide (100 mg/dose) every other day by intravenous infusion. On the same day as the third dose of oligonucleotide, the patient is administered a chemotherapeutic agent. Additional rounds of chemotherapy or doses of oligonucleotide are administered as needed.

Methods for assessing the effectiveness of a treatment for cancer are known to one of skill in the art. For example, the effectiveness of the ERV-9 U3 oligonucleotide for treating the cancer can be assessed by measuring tumor size, tumor cell volume, number of tumor metastases, or tumor recurrence. A decrease (for example, at least about a 10%, 20%, 30%, 40%, 50%, 60%, 70%, 80%, 90%, 95%, 98%, 99%, or even 100% decrease) in tumor size, cell volume, metastasis, or recurrence indicates that treatment with the ERV-9 U3 oligonucleotide is effective for treating This disclosure provides oligonucleotides that specifically target the ERV-9 LTR. The disclosure further provides methods of treating a subject diagnosed with cancer with the oligonucleotides disclosed herein. It will be apparent that the precise details of the methods described may be varied or modified without departing from the spirit of the described disclosure. We claim all such modifications and variations that fall within the scope and spirit of the claims below.

The invention claimed is:

1. An isolated oligonucleotide analog, a modified oligonucleotide or a labeled oligonucleotide, wherein the nucleotide sequence of the oligonucleotide is at least 90% identical to SEQ ID NO: 1 or at least 90% identical to SEQ ID NO: 2.

2. A composition comprising the oligonucleotide analog, modified oligonucleotide or labeled oligonucleotide of claim 1 and a pharmaceutically acceptable carrier.

3. The oligonucleotide analog, modified oligonucleotide or labeled oligonucleotide of claim 1, wherein the nucleotide sequence of the oligonucleotide is at least 95% identical to SEQ ID NO: 1 or at least 95% identical to SEQ ID NO: 2.

4. The oligonucleotide analog, modified oligonucleotide or labeled oligonucleotide of claim 1, wherein the nucleotide sequence of the oligonucleotide comprises SEQ ID NO: 1 or comprises SEQ ID NO: 2.

5. The oligonucleotide analog or modified oligonucleotide of claim 1, comprising at least one modified internucleoside linkage, at least one modified sugar moiety or at least one modified base.

6. The labeled oligonucleotide of claim 1, comprising a radioisotope, fluorophore or enzyme.

7. The modified oligonucleotide of claim 1, comprising phosphorothioate internucleoside linkages at each position.

8. An isolated oligonucleotide comprising a small interfering RNA, wherein the siRNA comprises an oligonucleotide analog, modified oligonucleotide or labeled oligonucleotide at least 80%, at least 85%, at least 90% or at least 95% identical to SEQ ID NO: 13 and an oligonucleotide analog, modified oligonucleotide or labeled oligonucleotide at least 80%, at least 85%, at least 90% or at least 95% identical to SEQ ID NO: 14.

9. A composition comprising the oligonucleotide of claim 8 and a pharmaceutically acceptable carrier.

10. The oligonucleotide of claim 8, wherein the siRNA comprises an oligonucleotide analog, modified oligonucleotide or labeled oligonucleotide at least 95% identical to SEQ ID NO: 13 and an oligonucleotide analog, modified oligonucleotide or labeled oligonucleotide at least 95% identical to SEQ ID NO: 14.

11. The oligonucleotide of claim 8, wherein the siRNA comprises an oligonucleotide analog, modified oligonucleotide or labeled oligonucleotide comprising SEQ ID NO: 13 and an oligonucleotide analog, modified oligonucleotide or labeled oligonucleotide comprising SEQ ID NO: 14.

12. A method of treating a subject having a cancer associated with expression of human endogenous retrovirus (ERV)-9 long terminal repeat (LTR) RNA, comprising selecting a subject in need of such treatment and administering to the subject a therapeutically effective amount of a first therapeutic agent, wherein the first therapeutic agent comprises the oligonucleotide analog, modified oligonucleotide or labeled oligonucleotide of claim 1, thereby treating the subject with cancer.

13. The method of claim 12, wherein the nucleotide sequence of the oligonucleotide analog, modified oligonucleotide or labeled oligonucleotide comprises the sequence shown in SEQ ID NO: 1 or SEQ ID NO: 2.

14. The method of claim 12, wherein the cancer is selected from breast cancer, liver cancer, prostate cancer, fibrosarcoma, and myeloid cancer.

15. The method of claim 12, further comprising administering to the subject a second therapeutic agent.

16. The method of claim 15, wherein the second therapeutic agent is an antisense compound or a chemotherapeutic agent.

17. The method of claim 16, wherein the antisense compound is an antisense oligonucleotide specific for Bcl-2, telomerase or MDM2.

18. A method of detecting expression of ERV-9 RNA in a sample obtained from a subject diagnosed with cancer, comprising:
   isolating RNA from the sample;
   contacting the isolated RNA with the oligonucleotide analog, modified oligonucleotide or labeled oligonucleotide of claim 1; and
   detecting hybridization of the oligonucleotide to the isolated RNA, wherein hybridization of the oligonucleotide to the isolated RNA indicates ERV-9 RNA is expressed in the sample.

19. The method of claim 18, wherein the sample is a tissue sample or bodily fluid sample.

20. The method of claim 19, wherein the tissue sample is a cancer tissue sample.

21. The method of claim 18, further comprising selecting a treatment for the subject diagnosed with cancer by detecting expression of ERV-9 RNA.

22. The method of claim 21, wherein the treatment comprises administering to the subject a therapeutically effective amount of at least one ERV-9 LTR oligonucleotide, wherein the at least one oligonucleotide is about 15 to about 40 nucleotides in length, and wherein the at least one oligonucleotide specifically hybridizes with the coding strand or the non-coding strand of the ERV-9 LTR.

23. The method of claim 18, wherein the cancer is selected from breast cancer, liver cancer, prostate cancer, fibrosarcoma and myeloid cancer.

\* \* \* \* \*

```
                         SEQUENCE LISTING

<160> NUMBER OF SEQ ID NOS: 22

<210> SEQ ID NO 1
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 1
ctcaaggttt gtaaacacac caatcag                                         27

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 2
ctgattggtg tgtttacaaa ccttgag                                         27

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
cattatcaac aaaatactcc aatt                                            24

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
```
tctcccagcg tgcgccat                                               18

<210> SEQ ID NO 5
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 5
tagggttaga caa                                                    13

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
tgacacctgt tctcactcac                                             20

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
ccgagcctcg ccgacgagcg ccgc                                        24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
gcggcgctcg tcggcgaggc acgg                                        24

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 9
ggctggccaa ggccagagcc ggctcc                                      26

<210> SEQ ID NO 10
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 10
ccgaccggtt ccggtctcgg ccgagg                                      26

<210> SEQ ID NO 11
<211> LENGTH: 22
<212> TYPE: DNA
<213> ORGANISM: Artificial Sequence
<220> FEATURE:

<223> OTHER INFORMATION: Synthetic oligonucleotide

<400> SEQUENCE: 11
gaacacatcc aaacatcaga ac                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gttctgatgt ttggatgtgt tc                                              22

<210> SEQ ID NO 13
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 13
cucaagguuu guaaacacac caaucag                                         27

<210> SEQ ID NO 14
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 14
cugauuggug uguuuacaaa ccuugag                                         27

<210> SEQ ID NO 15
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 15
gccugauguu caaacaccug guaca                                           25

<210> SEQ ID NO 16
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 16
ccugugaagc ucauugggau gaauu                                           25

<210> SEQ ID NO 17
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 17
accaugauau cuggcagaug uauaa                                           25

<210> SEQ ID NO 18

```
<211> LENGTH: 1788
<212> TYPE: DNA
<213> ORGANISM: Homo sapiens
<220> FEATURE:
<221> NAME/KEY: misc_feature
<222> LOCATION: (80)..(1788)
<223> OTHER INFORMATION: ERV-9 LTR

<400> SEQUENCE: 18
ggagccttgc tcctggaaag actaactcag ggagccagaa gttatcctcc aggttgaggt      60
gagtgaggga aagagtggtt gtgagaggtg acagcgtgct ggcagtcctc acagccctcg     120
ctcgctctcg gcgcctcctc tgcctgggtc ccactttggc ggcacttgag gagcccttca     180
gcccactgct gcactgtggg agcccttttac ctgggctggc caaggccgga gccggctccc    240
tcagcttgca gggaggtgtg gagggagagg aaagagcggg aacccgggct gcacgcggca     300
cttgcgggcc agttggagtt cagagtgggc atgggcttgg cgggccccac actcggagca     360
gcccggccct gccggcccca ggcaatgagg ggcttagcac ccgggccagc ggctgcggag     420
ggtgtactgg gtcccccagc agggccagcc caccggcgct gcactcgatt tcttgctggg     480
ccttagctgc cttcccgtgg ggcagggctc ggacctgca gcccgccatg cctgagcctc      540
caaccccctg ggtgggctcc tgtacggccc gatcctcccc gatgagcgcc gccccctgct     600
ccaggcaccc agtcccatcg accacccaag ggctgaggag tgcgggtgca tgggcagga      660
ctggcaggca gctccacctg cagccccggt gcgggatcca ctgggtgaag ccagctgggc     720
ttctgagtct ggtggggaca tggagaacct ttatgtgtag ctcagggatt gtaaatacac     780
caatcagcac cctgtgctca gctcagggtt tgtgaatgca ccaatggaca ctctgtacct    840
agctactctg gtggggcctt ggagaacctt tatgtctagc tcagggattg taaatacact    900
gatcagcact ctgtatctag ctcaaggttt gtaaacacac caatcagcac ccgtgtctag    960
ctcagggttt gtgaatgcac caatctacac tctgtatcta gctactctgg tggggccttg   1020
gagaaccttt atgtctagct tcgagggatt gtaaatacac caatcggcac tctgtatctg   1080
actcaaggtt tgtaaacaca ccaatcagca ccctgtgtct agctcagggt ttgtgaatgc   1140
accaatggac actctgtatc tagctactct ggtggggact tagagaacct ttagtcaact   1200
ctgtgtctag ctaatctagt ggggacgtgg agaacctttg tgtctagctc aggaattgta   1260
aacacaccaa tcagcgccct gtcaaaaacag accaggcctc taccaatcag caggatgtgg   1320
gtggggccag ataagagaat gaaagcaggc tgccggagcc agcagtggca accgctgggg   1380
tcccttccca cactgtggaa gctttgttct ttcgctcttt gcaataaatc ttgctacttc   1440
tcactctttg ggtccacact gcttttacca gctgtaacac tcaccgcaaa cgtctgcagc   1500
ttcactcctg aagccagcga gaccacgagc ccaccgggag gaacgaacaa ctccagacgc   1560
gccgccttaa gccttaagag ctgtaacact caccacgaag gtctgcagct tcactcctga   1620
gccagcgaga ccacgaaccc gccagaagga agaaactccg aacacatccg aacatcagaa   1680
ggaacaaact ctagacgcgc caccttaaga gctgtaacac tcaccacaag ggtccgcggc   1740
ttcattcttg aagtcagtga gaccaagaac ccaccaattc cggacaca                1788

<210> SEQ ID NO 19
<211> LENGTH: 8137
<212> TYPE: DNA
<213> ORGANISM: Homo sapiens
<220> FEATURE:
<221> NAME/KEY: misc_feature
<222> LOCATION: (2660)..(4349)
<223> OTHER INFORMATION: ERV-9 LTR
```

<400> SEQUENCE: 19

```
agatcctcac atgagttcag tatataattg taacagaata aaaaatcaat tatgtattca      60
agttgctagt gtcttaagag gttcacattt ttatctaact gattatcaca aaaatacttc     120
gagttacttt tcattataat tcctgactac acatgaagag actgacacgt aggtgcctta     180
cttaggtagg ttaagtaatt tatccaaaac cacacaatgt agaacctaag ctgattcggc     240
catagaaaca caatatgtgg tataaatgag acagagggat ttctctcctt cctatgctgt     300
cagatgaata ctgagataga atatttagtt catctatcac acattaaacg ggactttaca     360
tttctgtctg ttgaagattt gggtgtggga taactcaagg tatcatatcc aagggatgga     420
tgaaggcagg tgactctaac agaaagggaa aggatgttgg caaggctatg ttcatgaaag     480
tatatgtaaa atccacatta agcttctttc tgcatgcatt ggcaatgttt atgaataatg     540
tgtatgtaaa agtgtgctgt atattcaaaa gtgtttcatg tgcctagggg tgtcaaatac     600
tttgagtttg taagtatata cttctctgta atgtgtctga atatctctat ttacttgatt     660
ctcaataagt aggtatcata gtgaacatct gacaaatgtt tgaggaacaa tttagtgttt     720
acctattcac caaaatttat taaatgccta atctgtatca gatatacaat tatctggcga     780
aatctgtaat tcctaattta aacagctgtg tagcctaatt agggataaag gcatgcaaac     840
ccataatttg tgtaggttga aatgagctat agaaaaatgc agtatattta tcagaagtct     900
ttagggtcat gaaaaggaat ggtcaactga cactgccagg gactcatatg taagagataa     960
ctaatgtgaa gtgactttaa aggagaaatt agcagaagtt ttctttccat gtctcctcat    1020
catgttacaa taacggaaga gattaaaaca acaaatacat ttagacagca atgtttatcc    1080
tggttagatg tttaatcta aatctatctt ggagtgttaa aatgcatttg ctcacctact    1140
ttaaaatata aatgaaggta ggaacctgta gatacaaaaa gttggagaaa aaaagacaat    1200
aaagatgaca aaaatctatt aatccttgat agaaaatgag aagagataaa acactggttt    1260
acataaagaa aataagatgg atagatagca gatccttata aaagtgataa tttgagaaaa    1320
aaaatactcc atattctgag tttcttcaca taaaataata caaatctgct gtggtaagtt    1380
acaaagagat agatttttat cattatataa aagatatttt aaacagagtt atacaacaaa    1440
ggaacagact atgtcatata ttctcactta tcactataaa catctcagaa aaatctgcaa    1500
aatcatttca tagcattta aatagttagg aataatgtag aaaactgaaa cagttctaag    1560
tttcccacaa acttagagtc tcaaatgttg cattacctaa cttacctgca aatatttat    1620
acaaatttgc acatgctact ctagtcaaaa atatatgtac attatgggta ttttctgtgt    1680
gtaacttggt tctagttgct tctttcagaa atagcctcta ttttgattt acctgataaa    1740
atcacattcc tctccaaagc cttctaaata cttccagact aactacttt tagtacatct    1800
aagaagaaaa gagttttgtc tcttatccac ctctgagtca aaaagcagca tgtccatcaa    1860
ttggtacata gttcccacag ccccacttag ctctggattg gagttctact tggcattgtt    1920
tgcaactaca tggacgtaaa atgcatggat tctcttgaaa aaatgtttct gccatgatgt    1980
tctctgaaag agactaacct tccctcgctt tgcagagaaa gactcgtgta atccttgaca    2040
atgtcatctc atctatttat tcccatgtct acccatatgt gaccttcatg tctttgtctc    2100
aagcccctac atcctcaatc tacacactag gatagtataa aagtaatagt aataatagta    2160
gtaatagtaa taacaataca atgattatgg cttatactat acacaagaca ctgttgatat    2220
attatttcat ttagtattca cagtaactct gtgcctcaag tactattgta ataccccttta   2280
agaggaggaa actgaggcac agggccctaa agtaatattc caagatgaag tggctactaa    2340
```

```
ctgacagagg gcataattca actcatgata tttggctcta gaatacatgc tctgaatcat    2400
tatacaataa taattcatga ggaaacattt tttaaagcct aagttatttg ctctgaaata    2460
agacataatt tggggtgaga aagcttagat tccatgaagt attacagcat tggtagtct     2520 ttttgcactc caggtcttat ttttactgct taaacataat aaaacatatg gttcagtatg    2580
cctttgattt tacaataata ttcctgttat ttttggaagc acagggtgtg ggataatgct    2640
aattactagt gattagtatt gagaggtgac agcgtgctgg cagtcctcac agccctcgct    2700
cgctcttggc gcctcctctg cctgggctcc cacattggtg gcacttgagg agcccttcag    2760
ccggccgctg cactgtggga gccctttttct gggctggcca aggccagagc cggctccctc   2820
agcttgccag gaggtgtgga gggacagacg cgggcaggaa ccgggctgtg cgccgtgctt    2880
gagggagttc cgggtgggca tgggctccga ggaccccgca ctcggagccg ccagccggcc    2940
ccaccggccg cgggcagtga ggggcttagc acctgggcca gcagctgctg tgctcaattc    3000
ctcgccgggc cttagctgcc ttcctgcggg gcagggctcg ggacctgcag cgcgccatgc    3060
ctgagcctcc ccaccttcat gggctcctgt gcggcccgag cctcgccgac gagcgccgcc    3120
ccctgctcca gggcacccag tcccatcgac cacccaaggg ctgaagagtg cgggcgccag    3180
caaggggact ggcaggcagc tcccccctgca gcccaggtgc gggatccact gggtgaagcc    3240
ggctaggtcc tgagtttgct ggggatgcga agaaccctta tgtctagata agggattgta    3300
aatacaccaa ttggcactct gtatctagct caaggtttgt aaacacacca atcagcaccc    3360
tgtgtctagc tcagggtttg tgaatgcacc aatcaacact ctatctagct actctggtgg    3420
ggccttggag aacctttatg tctagctcag ggattgtaaa tacaccaatc ggcagtctgt    3480
atctagctca aggtttgtaa acacaccaat cagcaccctg tgtctagctc agggtttgtg    3540
aatgcaccaa tcaacactct gtatctagct actctggtgg ggacgtggag aacctttatg    3600
tctagctcag ggattgtaaa taccactc ggcagtctgt atctagctca aggtttgtaa     3660
acacaccaat cagcaccctg tgtctagctc agggtttgtg aatgcaccaa tcaacactct    3720
gtatctagct actctggtgg gacttggaga acctttgtgt ggacactctg tatctagcta    3780
atctggtggg gacgtggaga acctttgtgt ctagctcatg gattgtaaat gcaccaatca    3840
gtgccctgtc aaaacagacc actgggctct ctaccaatca gcaggatgtg ggtggggcca    3900
gataagagaa taaaagcagg ctgcccgagc cagcagtggc aacccgctcg ggtcccctcc    3960
cacactgtgg aagctttgtt ctttcgctct ttgcaataaa tcttgctgct gctcactgtt    4020
tgggtctaca ctgcctttat gagctgtaac gctaccgcg aagtctgca gcttcactct     4080 tgaagccagc gagaccacga acccaccgga ggaacgaaca actccagagg cgccgcttaa    4140
gagctggaac gttcactgtg aaggtctgca gcttcactcc tgagccagcg agaccacgaa    4200
cccatcagaa ggaagaactc gaacacatcc aaacatcaga acgaacaact ccacacacgc    4260 agccttaag aactgtaaca ctcaccacga gggtccccgg cttcattctt gaagtcagtg      4320
aaaccaagaa cccaccaatt ccggacacag tatgtcagaa acaatatgag tcactaaatc    4380
aatatacttc tcaacaattt ccaacagccc ttgcaattaa cttggccatg tgactggttg    4440
tgactaaaat aatgtggaga taataatgtg ttactcccta aggcagagtg cccttctatc    4500
attctctttc ccttcctcta tgtggcagaa agtaaaagat tctgaaatga taaagtcaat    4560
cacaggaagg cacctggact cctggcccac tgcttggagg agagcactca ggaccatgaa    4620
catctgactg tgacgtagca ataaagaaac ccacgtttca tatgaaactg cttaaaatta    4680
atggcacaag tcatgttttt gatgttgcac atttgtcttt atttgtggct tgttttgctt    4740
```

```
ccacatcaat ccactcaagg cctacattct gctataatgc aatttcaagt tctttacagg    4800
ccgagaaaaa tgaatctgaa ttcctgacct ccaaaagtga tcaagatatt tttagttcag    4860
gctccaaaat tttctcattt tcataggttt tcctcgattg atcattattc atgatttgca    4920
aggaatcatt caatgttttc taaatctatt actgcatcct gacacatatg acattttaac    4980
tatgttccag attttgaat gaagagtgta aattttaaat gttttcacca caaaaataa    5040
gtatgtgaag tggtggattt gttaattagc cttatttaac catttaatat tgtacacgta    5100
caccaaagca tcatgttgta ccccatgaat acacacaatt attatttgtc aatttaaaat    5160
gaaataataa aaaataacaa agcattagcc tctgcattgc ctttaccggt catctcacgg    5220
tgactaacgc aaaaacgttc tatttcatcc ttacaaacat ccctatcttt gatgcctctt    5280
tgtctagatc tctatcccct cctgttttct ctacgttatt tatatgggta tcatcacatc    5340
ctggacaaca tcaggacaga tatccctcac caagccaatg ttcctctcta tgttggctca    5400
aatgtccttg aactttcctt tcaccaccct ttccacagtc aaaaggatat tgtagtttaa    5460
tgcctcagag ttcagctttt aagcttctga caaattattc ttcctcttta ggttctcctt    5520
tatgaatct tctgtactga tggccatgtc ctttaactac tatgtagata tctgctacta    5580
cctgtattat gcctctacct ttattagcag agttatctgt actgttggca tgacaatcat    5640
ttgttaatat gacttgcctt tccttttct gctattcttg atcaaatggc tcctctttct    5700
tgctcctctc atttctcctg ccttcacttg gacgtgcttc acgtagtctg tgcttatgac    5760
tggattaaaa attgatatgg acttatccta atgttgttcg tcataatatg ggttttatgg    5820
tccattatta tttcctatgc attgatctgg agaaggcttc aatccttta ctctttgtgg    5880
aaaatatctg taaaccttct ggttcactct gctatagcaa gtttcagttt aggctagtaa    5940
gcatgaggat gcctccttct ctgatttttc ccacagtctg ttggtcacag aataacctga    6000
gtgattactg atgaaagagt gagaatgtta ttgatagtca caatgacaaa aaacaaacaa    6060
ctacagtcaa aatgtttctc tttttattag tggattatat ttcctgacct atatctggca    6120
ggactcttta gagaggtagc tgaagctgct gttatgacca ctagagggaa gaagatacct    6180
gtggagctaa tggtccaaga tggtggagcc ccaagcaagg aagttgttaa ggagcccttt    6240
tgattgaagg tgggtgcccc caccttacag ggacaggaca tctggatact cctcccagtt    6300
tctccagttt cccttttcc taatatatct cctgataaat gtctatactc acttccccat    6360
ttctaataat aaagcaaagg ctagttagta agacatcacc ttgcattttg aaaatgccat    6420
agctttcaaa attatttcat acatcggtct ttctttattt caagagtcca gaaatggcaa    6480
cattaccttt gattcaatgt aatggaaaga gctctttcaa gagacagaga aaagaataat    6540
ttaatttctt tccccacacc tccttccctg tctcttaccc tatcttcctt ccttctaccc    6600
tccccatttc tctctctcat ttctcagaag tatattttga aaggattcat agcagacagc    6660
taaggctggt ttttctaag tgaagaagtg atattgagaa ggtagggttg catgagccct    6720
ttcagttttt tagtttatat acatctgtat tgttagaatg ttttataata taaataaaat    6780
tatttctcag ttatatacta gctctgtaac ctgtggatat ttccttaagt attacaagct    6840
atacttaact cacttggaaa actcaaataa ataccctgctt catagttatt aataaggatt    6900
aagtgagata atgcccataa gattcctatt aataacagat aaatacatac acacacacac    6960
acattgaaag gattcttact ttgtgctagg aactataata agttcattga tgcattatat    7020
attgaagttc taatttcaac actagaaggc aggtattatc taaatttcat actggatacc    7080
tccaaactca caaagataat taaattgcct tttgtcatat atttattcaa aagggtaaac    7140
```

```
tcaaactatg gcttgtctaa ttttatatat caccctactg aacatgaccc tattgtgata      7200
ttttataaaa ttattctcaa gttattatga ggatgttgaa agacagagag gatggggtgc      7260
tatgccccaa atcagcctca caattaagct aagcagctaa gagtcttgca gggtagtgta      7320
gggaccacag ggttaagggg gcagtagaat tatactccca ctttagtttc atttcaaaca      7380
atccatacac acacagccct gagcacttac aaattatact acgctctata ctttttgttt      7440
aaatgtataa ataagtggat gaaagaatag atagatagat agacagatag atgatagata      7500
gaataaatgc ttgccttcat agctgtctcc ctaccttgtt caaaatgttc ctgtccagac      7560
caaagtacct tgccttcact taagtaatca attcctaggt tatattctga tgtcaaagga      7620
agtcaaaaga tgtgaaaaac aatttctgac ccacaactca tgctttgtag atgactagat      7680 caaaaattt cagccatatc ttaacagtga gtgaacagga aatctcctct tttccctaca       7740
tctgagatcc cagcttctaa gaccttcaat tctcactctt gatgcaacag accttggaag      7800
catacaggag agctgaactt ggtcaacaaa ggagaaaagt ttgttggcct ccaaaggcac      7860
agctcaaact tttcaagcct tctctaatct taaaggtaaa caagggtctc atttctttga      7920
gaacttcagg gaaaatagac aaggacttgc ctggtgcttt tggtaggggga gcttgcactt     7980 tcccccttct ggaggaaata tttatcccca ggtagttccc tttttgcacc agtggttctt      8040
tgaagagact tccacctggg aacagttaaa cagcaactac agggccttga actgcacact      8100
ttcagtccgg tcctcacagt tgaaaagacc taagctt                               8137

<210> SEQ ID NO 20
<211> LENGTH: 982
<212> TYPE: DNA
<213> ORGANISM: Homo sapiens

<400> SEQUENCE: 20
ttatgtctag ataagggatt gtaaatacac caattggcac tctgtatcta gctcaaggtt        60
tgtaaacaca ccaatcagca ccctgtgtct agctcagggt ttgtgaatgc accaatcaac       120
actctatcta gctactctgg tggggccttg gagaaccttt atgtctagct cagggattgt       180
aaatacacca atcggcagtc tgtatctagc tcaaggtttg taaacacacc aatcagcacc       240
ctgtgtctag ctcagggttt gtgaatgcac caatcaacac tctgtatcta gctactctgg       300
tggggacgtg gagaaccttt atgtctagct cagggattgt aaatacacca ctcggcagtc       360
tgtatctagc tcaaggtttg taaacacacc aatcagcacc ctgtgtctag ctcatggatt       420
gtaaatgcac caatcagtgc cctgtcaaaa cagaccactg ggctctacca atcagcagga       480
tgtgggtggg gccagataag agaataaaag caggctgccc gagccagcag tggcaacccg       540
ctcgggtccc cttccacact gtggaagctt tgttctttcg ctctttgcaa taaatcttgc       600
tgctgctcac tgtttgggtc tacactgcct ttatgagctg taacgctcac cgcgaaggtc       660
tgcagcttca ctcttgaagc cagcgagacc acgaacccac cggaggaac gaacaactcc       720 agaggcgccg ccttaagagc tggaacgttc actgtgaagg tctgcagctt cactcctgag       780
ccagcgagac cacgaaccca tcagaaggaa gaaactccga acacatccaa acatcagaac       840
gaacaaactc cacacacgca gcctttaaga actgtaacac tcaccacgag ggtccccggc       900
ttcattcttg aagtcagtga aaccaagaac ccaccaattc cggacacagt atgtcagaaa       960
caatatgagt cactaaatca at                                               982

<210> SEQ ID NO 21
<211> LENGTH: 23
<212> TYPE: DNA
```

```
<213> ORGANISM: Artificial Sequence
<220> FEATURE:
<223> OTHER INFORMATION: Synthetic oligonucleotide

<400> SEQUENCE: 21
cctgagtttg ctggggatgc gaa                                               23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 22
accctgagct agacacaggg tgc                                               23
```